US012644152B2

(12) United States Patent
Zhou et al.

(10) Patent No.: US 12,644,152 B2
(45) Date of Patent: Jun. 2, 2026

(54) HIGH THROUGHPUT ANALYSIS OF FIXED CELLS

(71) Applicant: Singleron Biotechnologies Inc., Woodbridge, CT (US)

(72) Inventors: Jing Zhou, Woodbridge, CT (US); Janaki Acharya, Woodbridge, CT (US)

(73) Assignee: Singleron Biotechnologies Inc., Woodbridge, CT (US)

( * ) Notice: Subject to any disclaimer, the term of this patent is extended or adjusted under 35 U.S.C. 154(b) by 0 days.

(21) Appl. No.: 17/388,537

(22) Filed: Jul. 29, 2021

(65) Prior Publication Data
US 2022/0033897 A1 Feb. 3, 2022

Related U.S. Application Data

(60) Provisional application No. 63/059,964, filed on Jul. 31, 2020, provisional application No. 63/184,712, filed on May 5, 2021.

(51) Int. Cl.
*C12Q 1/6874* (2018.01)
*C12Q 1/6876* (2018.01)

(52) U.S. Cl.
CPC ......... *C12Q 1/6874* (2013.01); *C12Q 1/6876* (2013.01); *C12Q 2600/158* (2013.01)

(58) Field of Classification Search
CPC ............ C12Q 1/6874; C12Q 2600/158; C12Q 1/6806; C12Q 2525/179; C12Q 2535/122; C12Q 2563/149; C12Q 2563/159; C12Q 2523/319; C12Q 2525/173; C12Q 2563/179
See application file for complete search history.

(56) References Cited

U.S. PATENT DOCUMENTS

| | | | | |
|---|---|---|---|---|
| 2019/0127731 A1 * | 5/2019 | McDermott | ......... | C12Q 1/6874 |
| 2019/0136316 A1 * | 5/2019 | Hindson | .............. | C12Q 1/6855 |

FOREIGN PATENT DOCUMENTS

| | | | | | |
|---|---|---|---|---|---|
| CA | 2989976 A1 * | 12/2016 | ......... | C12N 15/1065 |
| WO | WO-2014163886 A1 * | 10/2014 | .............. | C12P 19/34 |
| WO | WO-2017044893 A1 * | 3/2017 | ......... | C12N 15/1065 |
| WO | WO2017/095917 | 6/2017 | | |
| WO | WO2018/148700 | 8/2018 | | |
| WO | WO2018/226293 | 12/2018 | | |
| WO | WO-2019060771 A2 * | 3/2019 | .......... | C12Q 1/6806 |
| WO | WO2019/222284 | 11/2019 | | |
| WO | WO2020/037065 | 2/2020 | | |
| WO | WO2020/123309 | 6/2020 | | |
| WO | WO-2020056381 A9 * | 7/2020 | ............. | C07H 21/02 |
| WO | WO-2020198071 A1 * | 10/2020 | .......... | C12Q 1/6841 |
| WO | WO-2020198532 A1 * | 10/2020 | .......... | C12Q 1/6806 |
| WO | WO2021/041974 | 3/2021 | | |
| WO | WO-2021041953 A1 * | 3/2021 | ......... | A61K 38/1709 |
| WO | WO-2021081486 A2 * | 4/2021 | ....... | B01L 3/502761 |
| WO | WO2022/026667 | 2/2022 | | |
| WO | WO2022/251110 | 12/2022 | | |
| WO | WO2023/028582 | 3/2023 | | |

OTHER PUBLICATIONS

Cronin et al. American Journal of Pathology. 2004. 164(1):35-42. (Year: 2004).*
Ke et al. Nature Methods. 2013. 10(9):857-860. (Year: 2013).*
Masuda et al. Nucleic Acids Research. 1999. 27(22):4436-4443. (Year: 1999).*
Bagasra et al. Nature Protocols. 2007. 2(11):2782-2795. (Year: 2007).*
Lee et al. Nature Protocols. 2015. 10(3):442-458. (Year: 2015).*
Lee et al. Science. 2014. 343(6177):1360-1363. (Year: 2014).*
Alles et al., "Cell fixation and preservation for droplet-based single-cell transcriptomics," BMC Biology 2017, 15(44), in 14 pages.
Bose et al., "Scalable microfluidics for single-cell RNA printing and sequencing," Genome Biology 2015, 16(120), 1-16.
Brennecke et al., "Accounting for technical noise in single-cell RNA-seq experiments," Nature Methods 2013, 10(11), 1093-1095.
Cao et al., "Comprehensive single-cell transcriptional profiling of a multicellular organism," Science 2017, 357, 661-667.
International Search Report and Written Opinion dated Oct. 26, 2021 in PCT Application No. PCT/US2021/043643.
Islam et al., "Characterization of the single-cell transcriptional landscape by highly multiplex RNA-seq," Genome Research 2011, 21, 1160-1167.
Jaitin et al., "Massively parallel single cell RNA-Seq for marker-free decomposition of tissues into cell types," Science 2014, 343(6172), 776-779.

(Continued)

*Primary Examiner* — Joseph G. Dauner
(74) *Attorney, Agent, or Firm* — Dickinson Wright PLLC

(57) ABSTRACT

Methods and systems for the high throughput RNA profiling or sequencing analysis of fixed single cells are provided. The methods and systems utilize barcoded microcarriers comprising a small carrier bead attached to a plurality of molecular barcodes with cleavable linkers, wherein these barcoded microcarriers are then combined in a system (e.g., a sealed system) with a single cell. The molecular barcodes are then released from the carrier beads to anneal to the mRNAs in the cells. Using reverse transcription, barcoded cDNAs is then generated from the mRNAs and the cells are lysed or digested to release the barcoded cDNAs for sequencing.

19 Claims, 13 Drawing Sheets

(56)         References Cited

OTHER PUBLICATIONS

Klein et al., Droplet Barcoding for Single-Cell Transcriptomics Applied to Embryonic Stem Cells, Cell 2015, 161, 1187-1201.
Macosko et al., "Highly parallel genome-wide expression profiling of individual cells using nanoliter droplets," Cell 2015, 161(5), 1202-1214.
Rosenberg et al., "Single-cell profiling of the developing mouse brain and spinal cord with split-pool barcoding," Science 2018, 360, 176-182.
Tang et al., "mRNA-Seq whole-transcriptome analysis of a single cell," Nature Methods 2009, 6(5), 377-382.
Intent to Gant dated Apr. 9, 2023 in Europe Patent Application No. 21769211.0.
Office Action dated Nov. 9, 2023 in Europe Patent Application No. 21769211.0.
International Search Report and Written Opinion dated Sep. 26, 2022 in PCT Application No. PCT/US2022/030522.
International Search Report and Written Opinion dated Dec. 22, 2022 in PCT Patent Application No. PCT/US2022/075509.

* cited by examiner

Bulk RNA-seq

Single cell RNA-seq

1. Load fixed and permeabilized cells into microwell array

2. Load barcoded microbeas into microwell array

3. Seal the microwell array with a cover

1. One single cell & one barcoded microbead were sealed in a microwell

2. Barcodes were cleaved from the microbead, diffusing into the cell and then binding with the RNA in the cell. In-cell RT generates barcoded cDNA.

3. Cell was digested and barcoded cDNAs were released,

Microcarrier

Microcarrier Variants

Microcarrier Variants

HIGH THROUGHPUT ANALYSIS OF FIXED CELLS

CROSS-REFERENCE TO RELATED APPLICATIONS

This application claims the benefit under 35 U.S.C. § 119(e) to U.S. Provisional Patent Application No. 63/059,964, filed on Jul. 31, 2020, and U.S. Provisional Patent Application No. 63/184,712, filed on May 5, 2021. The content of these related applications is incorporated herein by reference in its entirety for all purposes.

BACKGROUND

Knowledge of an mRNA sequence provides useful information on the genomic DNA from which it was transcribed. By analyzing the entire collection of mRNA sequences in a cell, also known as the transcriptome, it is possible to profile the expression of all genes and determine cell type, function, and state implicated in normal physiology or diseases. This information can be highly cell specific in the cells and tissues of an organism, as well as in tumor cells. Therefore, it would be highly desirable to obtain such sequencing information on single cells from a sample of a multicellular tissue or tumor, or a sample comprising a complex combination of cells.

SUMMARY

Disclosed herein include a method for single-cell RNA profiling. The method can comprise:
  loading a plurality of fixed cells into a plurality of microwells;
  loading a plurality of barcoded microcarriers into the plurality of microwells, wherein at least 5% of the plurality of microwells each is loaded with one of the plurality of fixed cells and one of the plurality of barcoded microcarriers, and wherein each of the plurality of barcoded microcarriers comprises:
    a microbead,
    a plurality of molecular barcodes each comprising an identical cell barcode, a unique molecule identifier (UMI) different across the plurality of molecular barcodes, a PCR handle, and a poly-T sequence capable of hybridizing to poly-A tails of messenger ribonucleic acid (mRNA) targets of the plurality of fixed cells, and
    a plurality of releasable linkers each associated with the microbead and linked with one of the plurality of molecular barcodes;
  releasing the molecular barcodes from the microbeads in the microwells, thereby diffusing the molecular barcodes into the fixed cells and hybridizing the molecular barcodes to mRNA targets of the fixed cells;
  reverse transcribing the mRNA hybridized with the molecular barcode to generate barcoded complementary deoxyribonucleic acids (cDNAs);
  pooling the barcoded cDNAs from the plurality of microwells; and
  analyzing the barcoded cDNAs or products thereof.
  In some embodiments, the method further comprises sealing the plurality of microwells. Analyzing the barcoded cDNAs or products thereof can comprise sequencing the barcoded cDNA or products thereof to obtain sequence information.

In some embodiments, the method comprises amplifying the barcoded cDNAs and sequencing the amplified barcoded cDNAs or products thereof to obtain sequence information. Analyzing the barcoded cDNAs or products thereof can comprise determining an expression profile of each of the mRNA targets using a number of UMIs with different sequences associated with each of the mRNA targets in the sequencing information. In some embodiments, the expression profile comprises an absolute abundance of the mRNA targets, a relative abundance of the mRNA targets, or both. In some embodiments, analyzing the barcoded cDNAs comprises determining a number of amplified barcoded cDNAs of each of the mRNA targets using a number of UMIs with different sequences associated with each of the mRNA targets in the sequencing information.

In some embodiments, at least 10%, at least 15%, at least 25%, at least 50%, or at least 75% of the plurality of microwells each is loaded with one of the plurality of fixed cells and one of the plurality of barcoded microcarriers. In some embodiments, at least 80% of the plurality of microwells each is loaded with one of the plurality of fixed cells and one of the plurality of barcoded microcarriers. In some embodiments, at least 90% of the plurality of microwells each is loaded with one of the plurality of fixed cells and one of the plurality of barcoded microcarriers.

In some embodiments, the method further comprises generating the plurality of fixed cells using chemical fixation. The chemical fixation can comprise fixation using one or more crosslinking fixatives, one or more precipitating fixatives, one or more oxidizing agents, one or more Hepes-glutamic acid buffer-mediated organic solvent protection effect (HOPE) fixatives, or a combination thereof. The chemical fixation can comprise fixation using formaldehyde, paraformaldehyde, glutaraldehyde, methanol, glycerol, or a combination thereof. In some embodiments, the plurality of fixed cells comprises permeabilized cells.

The microbead can be a polymeric microbead. The microbead can be a gel microbead. In some embodiments, the gel microbead is degradable upon application of a stimulus, optionally wherein the stimulus comprises a thermal stimulus, a chemical stimulus, a biological stimulus, a photo-stimulus, or a combination thereof. In some embodiments, releasing the molecular barcodes from the microbeads comprises disrupting the gel microbead to release the molecular barcodes. The microbead can be a magnetic microbead.

The plurality of fixed cells can comprise eukaryotic cells, prokaryotic cells, cells infected with a virus, or a combination thereof.

In some embodiments, each of plurality of releasable linkers is releasably associated with the microbead, releasably linked with the one of the plurality of molecular barcodes, or both. In some embodiments, releasing the molecular barcodes from the microbeads comprises cleaving the releasable linkers. Cleaving the releasable linkers can comprise cleaving the releasable linkers by UV light, chemical cleavage, enzymatic cleavage, or a combination thereof.

In some embodiments, the 5' end of the molecular barcode is linked with the releasable linker. In some embodiments, the 3' end of the molecular barcode is linked with the releasable linker. In some embodiments, the molecular barcode comprises from the 5' end to the 3' end, the PCR handle, the cell barcode, the UMI, and the poly-T sequence. In some embodiments, the molecular barcode comprises from the 5' end to the 3' end, the PCR handle, the UMI, the cell barcode, and the poly-T sequence. In some embodiments, the PCR handle and the poly-T sequence are at opposing ends of the molecular barcode. In some embodiments, the poly-T sequence is at the 3' end of the molecular barcode.

In some embodiments, reverse transcribing the mRNA hybridized with the molecular barcode to generate barcoded cDNAs is performed without lysing or digesting the cells. In some embodiments, the method further comprises lysing or digesting the fixed cells after the barcoded cDNAs are generated and before pooling the barcoded cDNAs from the plurality of microwells.

In some embodiments, sealing the plurality of microwells comprises sealing the plurality of microwells with a physical structure. The physical structure can comprise a film, a membrane, a glass slide, or a combination thereof. In some embodiments, sealing the plurality of microwells comprises sealing the plurality of microwells with an oil. The oil can comprise a fluorinated hydrocarbon oil. In some embodiments, each of the plurality of microbead has a diameter of about 10 μm to about 70 μm. In some embodiments, each of the plurality of microwells has a diameter (width) of about 10 μm to about 100 μm. In some embodiments, the plurality of microwells comprises about 1,000 microwells to about 500,000 microwells. In some embodiments, barcoded cDNAs from about 100 cells to about 50,000 cells are analyzed.

Also provided herein include a system for performing any high throughput single-cell mRNA profiling method disclosed herein. The system can, for example, comprise: a) a microwell array comprising the plurality of microwells; b) a plurality of barcoded microcarriers; c) a means for sealing the microwell array; d) a means for cleaving the releasable linkers to release the molecular barcodes from the microbeads; and e) a means for generating the barcoded cDNAs. The system can further comprise, for example, one or more of f) a means for lysing or digesting the cells to release the barcoded cDNAs; g) a means for collecting the barcoded cDNAs; and h) a means for sequencing the barcoded cDNAs or the amplified barcoded cDNAs.

Provided herein includes a platform of Multiplexing by Cleavage, Delivery, and Barcoding (MX-CDB) used for single-cell analysis (e.g., single cell RNA sequencing). This platform provides a simplified and widely adoptable workflow that greatly improves microwell-based scRNA-seq applications to capture and mark mRNA from thousands of single cells of fixed biological samples and for preparation for sequencing.

Provided herein also include high throughput single-cell mRNA profiling methods. These methods comprise loading fixed and permeabilized cells and barcoded microcarriers (i.e., barcoded microbeads) into a microfluidic device with a microwell array substrate, wherein the molecular barcodes having the ability to be released from the microcarriers and bind to mRNA of cells. In some embodiments, the microwell array is then sealed, for example by a cover, to produce a sealed microwell array comprising the loaded cells and the barcoded microbeads. The molecular barcodes are released from the microcarriers and allowed to diffuse into the cells to capture and barcode the mRNAs of the cells. A reverse transcription reaction is performed to convert the barcoded mRNAs to barcoded cDNAs. The cells are lysed or digest to release the barcoded cDNAs which can be further sequenced. In another aspect, the methods are suitable for the analysis of the absolute abundances of mRNAs in the same cell and the relative abundances of mRNA for comparison between different cells.

Some embodiments disclosed herein provide: a high throughput single-cell RNA profiling method, the method comprising: (a) loading into a microwell array fixed cells having the mRNAs to be profiled and barcoded microcarriers, wherein said barcoded microcarriers comprise a microbead, a plurality of linkers, and a plurality of molecular barcodes, wherein the molecular barcode comprises a 5' end and a 3' end and further comprises a PCR handle, a cell barcode, a unique molecular identifier (UMI), and a poly-T sequence, such that the molecular barcode is cleavable and released from the microbead when the linker is cleaved, and wherein the released molecular barcode presents a poly-T sequence at its 3' end; (b) sealing the microwell array comprising the fixed cells and the barcoded microcarriers; (c) cleaving the linkers to release the molecular barcodes from the microbead to thereby diffuse into the fixed cell for the molecular barcodes to bind to the mRNAs to be profiled; (d) generating barcoded cDNAs by reverse transcription of the mRNAs with the molecular barcodes; (e) lysing or digesting the cells to release the barcoded cDNAs; (f) collecting the barcoded cDNAs; and (g) sequencing the barcoded cDNAs.

In some embodiments, the cells are permeabilized cells. In some embodiments, the microbeads are polymeric microbeads. In some embodiments, the microbeads are magnetic microbeads. In some embodiments, the PCR handle and the poly-T sequence are at opposing ends of the molecular barcode. This would also be the case when the molecular barcode is released that it has the PCR handle and the poly-T sequence at opposing ends. In some embodiments, the linker links the microbead to the 5' end of the molecular barcode, said molecular barcode comprising from the 5' end to the 3' end, a PCR handle, a cell barcode, a UMI, and a poly-T sequence. In some embodiments, the linker links the microbead to the 3' end of the molecular barcode, said molecular barcode comprising from the 5' end to the 3' end, a PCR handle, a cell barcode, a UMI, and a poly-T sequence. In some embodiments, the linker links the microbead to the 5' end of the molecular barcode, said molecular barcode comprising from the 5' end to the 3' end, a PCR handle, a UMI, a cell barcode, and a poly-T sequence. In some embodiments, the linker links the microbead to the 3' end of the molecular barcode, said molecular barcode comprising from the 5' end to the 3' end, a PCR handle, a UMI, a cell barcode, and a poly-T sequence. In some embodiments, microwell array is sealed with an oil.

In some embodiments, the microcarrier beads have a diameter from about 10 μm to about 70 μm. In some embodiments, the microwell array comprises microwells having a diameter (width) of from about 10 μm to about 100 μm. In some embodiments, the microwell array comprises from about 1,000 microwells to about 500,000 microwells. In some embodiments, about 100 cells to about 50,000 cells are processed simultaneously. In some embodiments, the microwell array is loaded with a well occupancy of about 5% to about 20%. In some embodiments, greater than about 80% of the microwells of the array comprise single barcoded microcarriers. In some embodiments, greater than about 90% of the microwells of the array comprise single barcoded microcarriers. In some embodiments, the cleavable linker is cleaved by UV light. In some embodiments, the cleavable linker is cleaved enzymatically.

Some embodiments include a system for performing the high throughput single-cell mRNA profiling method disclosed herein. In some embodiments, the system comprises (a) a microwell array; (b) barcoded microcarriers, wherein said barcoded microcarriers comprise a microbead, a plurality of linkers, and a plurality of molecular barcodes, wherein the molecular barcode comprises a 5' end and a 3' end and further comprises a PCR handle, a cell barcode, a unique molecular identifier (UMI), and a poly-T sequence, such that the molecular barcode is cleavable and released from the microbead when the linker is cleaved, and wherein the released molecular barcode presents a poly-T sequence at its 3' end; (c) a means for sealing the microwell array; (d) a means for cleaving the linker to release the molecular barcode from the microcarrier bead to thereby diffuse into the fixed cell for the molecular barcode to bind to the mRNA to be profiled; (e) a means for generating barcoded cDNA by reverse transcription of the mRNA to be profiled; and (f) a means for lysing or digesting the cells to release the barcoded cDNA. In some embodiments, the system further comprises (g) a means for collecting the barcoded cDNA, or (h) a means for sequencing the barcoded cDNA, or both.

Details of one or more implementations of the subject matter described in this specification are set forth in the accompanying drawings and the description below. Other features, aspects, and advantages will become apparent from the description, the drawings, and the claims. Neither this summary nor the following detailed description purports to define or limit the scope of the inventive subject matter.

BRIEF DESCRIPTION OF THE DRAWINGS

FIG. 5A shows the barcoded microcarrier of FIG. 4, and FIG. 5B shows a variant in which the same molecular barcode of FIG. 5A is linked to the bead at its opposite end. FIGS. 5C and 5D show additional variations where the positions of the cell barcode and UMI have been exchanged as compared to FIGS. 5A and 5B, respectively.

Figure 1A:
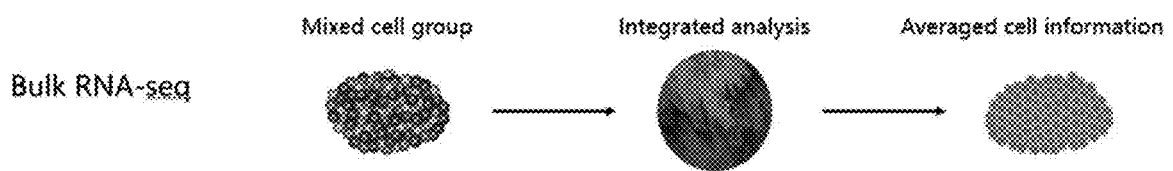
FIGS. 1A and 1B provide an illustrative comparison of the bulk RNA sequencing (FIG. 1A) versus the single cell RNA sequencing (FIG. 1B).

Throughout the drawings, reference numbers may be re-used to indicate correspondence between referenced elements. The drawings are provided to illustrate example embodiments described herein and are not intended to limit the scope of the disclosure.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Definitions

The term "microcarrier" as used herein means a construct comprising a carrier microbead (e.g., a small carrier bead), attached to one or more of a desired unique oligonucleotide sequence (e.g., a molecular barcode), via, for example, a cleavable linker.

The term "barcoded microcarrier" as used herein means a microcarrier comprising a molecular barcode, or alternatively, a unique oligonucleotide sequence comprising at least a PCR handle, a cell barcode, a unique molecular identifier (UMI), and a poly-T sequence.

The term "molecular barcode" as used herein means an oligonucleotide included in a barcoded microcarrier via a cleavable linker to identify a polynucleotide. The molecular barcode can be used to identify a sequence as being from a specific cell (cell barcode) or to a specific RNA strand (Unique Molecular Identifier; UMI). In the methods of the present invention, the molecular barcode further comprises elements for PCR amplification, such as a PCR handle, and a poly-T sequence for annealing to a mRNA sequence. The molecular barcode preferably comprises at least a PCR handle, a cell barcode, a unique molecular identifier (UMI), and a poly-T sequence. The molecular barcodes disclosed herein have the PCR handle and poly-T sequences at opposing ends of the sequence, for example with the PCR handle at the 5' end and the poly-T sequence at the 3' end. Either the poly-T sequence or the PCR handle can be linked to the microbead via the linker. The cell barcode and unique molecular identifier (UMI) need not be in a particular order so long as they are located between the opposed PCR handle and poly-T sequence.

The term "unique oligonucleotide sequence", or alternatively, "oligonucleotide sequence" or "oligonucleotide", as used herein means an oligonucleotide sequence meeting the definition of a "molecular barcode" as used herein.

The term "cell barcode" as used herein means a nucleotide sequence of the molecular barcode specific to the microbead to which it is attached. In the methods of the present invention wherein a single cell is isolated with the microbead, the cell barcode can be used to identify the corresponding single cell of the subsequently PCR amplified and sequenced nucleotides.

The term "cleavable linker" as used herein means a cleavable chemical linking moiety or a cleavable nucleotide sequence with a specific sequence connecting the microbead to the molecular barcode. The linker is cleavable, i.e. a cleavable linker, in order to release the molecular barcode from the microbead. The cleavable linker can be cleaved via any appropriate method or treatment, including but not limited to chemically, enzymatically, with light, including UV, visible, and near-infrared wavelengths, with mechanical force, and with heat.

The term "fixed cell" as used herein, means that the cell has been treated with a fixative such as a formaldehyde solution, which is also known as a formalin.

The term "microbead" as used herein means a carrier bead that generally has a diameter in the micrometer range, for example about 10 μm to about 70 μm, and to which the molecular barcode is attached via a cleavable linker.

The term "Multiplexing by Cleavage, Delivery, and Barcoding", abbreviated as "MX-CDB" refers to the methods and systems of the present invention for high throughput single cell analysis of fixed cells.

The term "PCR handle" as used herein means a nucleotide sequence included for the purpose of primer attachment and PCR amplification.

The term "permeable" as used herein, means that the cell is permeable to or porous to allow the transfer of materials, such as oligonucleotides, into the cell for annealing to the RNA within the cell.

The term "single cell sequencing" as used herein, refers to a method for obtaining sequence information from individual cells. The term Single-cell RNA-sequencing (scRNA-seq), as used herein, refers to this single cell sequencing method for RNA, such as messenger RNA (mRNA).

The term "poly-T" as used herein means a nucleotide sequence comprising sequential thymine nucleotides for annealing to mRNA nucleotides of the cell. In the methods of the present invention, the poly-T sequence is at either end of the molecular barcode and anneals the molecular barcode to the mRNA nucleotides of the cell after the cleavable linker has been cleaved.

The term "unique molecular identifier", abbreviated as UMI, means a nucleotide sequence of the molecular barcode specific to the RNA sequence to which the molecular barcode binds via its poly-T sequence. In the methods of the present invention, the UMI can be used to identify the RNA strand to which a given molecular barcode binds, following subsequent PCR amplification and sequencing analysis. In another aspect, the UMI is a molecular tag used to detect and quantify unique mRNA transcripts.

Figure 1B:
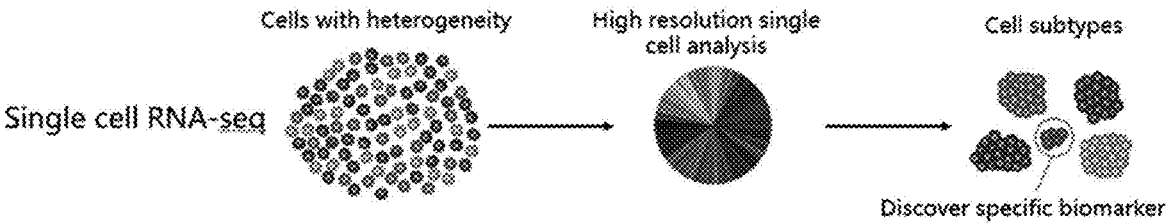

Single-cell RNA-sequencing (scRNA-seq) is becoming an important tool to investigate the heterogeneity of cells in complex biological samples and for classifying the subtypes of these cells. A comparison of bulk sequencing and single cell sequencing is shown in FIGS. 1A and 1B. FIG. 1A shows that bulk RNA sequencing on a mixed cell group provides averaged genomic information from all cells. On the contrary, single cell sequencing can extract the genomic information from each individual cell (FIG. 1B). Therefore, it is highly desirable to conduct single-cell RNA-sequencing, for example in a clinic setting.

Over the past two decades, there have been advances in the field of single cell isolation and genetic sequencing. These techniques for single cell isolation have ranged from manual isolation of single cells, multiplexing of samples utilizing multiwell sample plates, integrated fluidic circuits, liquid handling robotic systems, the incorporation of cells into droplets, and the use of extremely small picowells. The other direction some researchers have taken is the use of in situ barcoding of mixed cellular samples and the separation of individual cellular genetic data by complex data analysis techniques. With the assistance of microfluidics and highly diverse molecular barcoding techniques, it is possible to sequence thousands of cells and identify genetic information of each cell simultaneously with low cost. However, most of the technologies are only applicable to living cells, which hinders the advance of scRNA-seq to medical applications.

Current high throughput scRNA-seq technologies usually require working with fresh and highly viable cells, which means the collected samples have to been processed immediately once they are obtained. This requirement introduces greater difficulty for sample collection, transportation, and storage, and can also increase the costs associated with applying the high throughput scRNA-seq technology to medical samples. Therefore, it would be highly desirable to develop a single cell technology that can be used on fixed cells, such as samples that have been treated with a fixative such as formaldehyde. Such methods and systems for the high throughput RNA profiling or sequencing analysis of fixed single cells are disclosed herein. The methods and systems utilize barcoded microcarriers comprising a small carrier bead attached to a plurality of molecular barcodes with cleavable linkers, wherein these barcoded microcarriers are then combined in a sealed system with a single cell. The molecular barcodes are then released from the carrier beads to anneal to the mRNAs in the cells. Using reverse transcription, barcoded cDNAs are then generated from the mRNAs and the cells are lysed or digested to release the barcoded cDNAs for sequencing.

Platform

The present disclosure provides a Multiplexing by Cleavage, Delivery, and Barcoding platform for capturing mRNAs in fixed cells. This technique, referred to herein as MX-CDB scRNA-seq, uses a barcoded microcarrier to deliver molecular barcodes to fixed single cells isolated in microwells. The molecular barcodes comprising cell barcodes and UMIs can capture the mRNAs of fixed single cells for transcriptome sequencing. This method does not require fresh biological samples and can reduce the cost for sample collection, transportation, and storage. This technique is also compatible with a portable microfluidic device and does not require any special equipment, making it convenient for sample handling. The final products collected from the microfluidic devices are cDNAs in liquid solution. Compared to other scRNA-seq methods, the final products are stable and easy to retrieve.

Current high throughput scRNA-seq technologies usually require working with fresh and highly viable cells, which means the collected samples have to be processed immediately once they are obtained. This requirement introduces greater difficulty on sample collection, transportation, and storage, and can also increase the cost of applying the high throughput scRNA-seq technology to medical samples.

In comparison, fixation of cells (e.g., formaldehyde solution fixation of cells or methanol fixation of cells) is an easy, low cost, and widely accepted method for biological sample storage. For example, once biological samples are fixed by formaldehyde solution, they can be conveniently transported with less care and can be stored for a long time. The ability of the MX-CDB scRNA-seq method and systems disclosed herein to work with a fixed sample (e.g., a formaldehyde or methanol fixed sample) makes it compatible with medical samples. Also, most of the current scRNA-seq technologies use microbeads to deliver molecular barcodes to capture the mRNAs released from cells. The efficiency of retrieving barcoded microbeads from microfluidic devices can determine the quality of data. The existence of microbeads in the following molecular biology reactions, e.g., PCR amplification, etc., can inhibit the reaction efficiency. Herein, the MX-CDB scRNA-seq methods and systems disclosed herein more simply require retrieval of the molecular barcodes from the liquid of the microfluidic devices. This retrieval not only simplifies the workflow, but also improves the efficiency of mRNA captured and the quality of the sequencing data. Furthermore, for most of the scRNA-seq methods, when collecting the barcoded microbeads from the microfluidics, the microbeads usually capture the mRNAs of the cells. Such mRNA is relatively fragile and can be easily degraded during the process if it is not handled with extra care. In contrast, with the MX-CDB scRNA-seq methods and systems disclosed herein, the collected products from the microfluidics are already in the cDNA form, which is more stable and easier to handle and store than mRNA.

Barcoded Microcarrier

Figure 4:
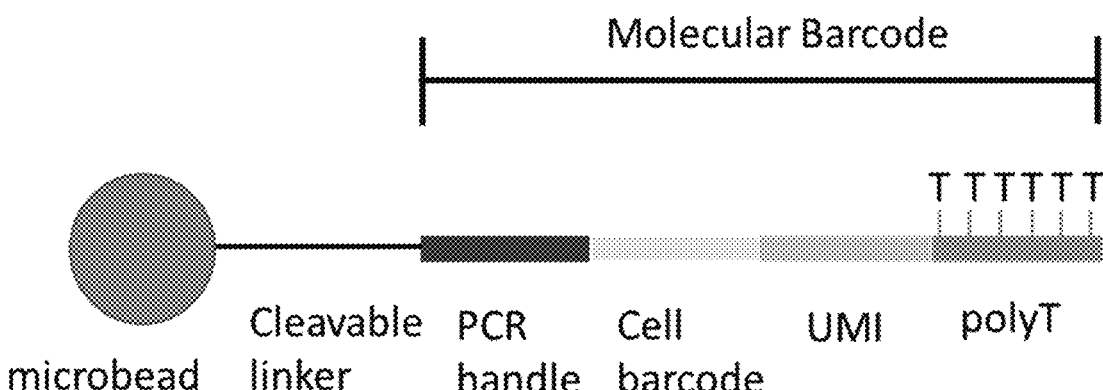
FIG. 4 shows a non-limiting schematic representation of a barcoded microcarrier disclosed herein with a molecular barcode attached via a cleavable linker. Shown left to right are a microbead, a cleavable linker, and a molecular barcode, wherein the molecular barcode comprises a PCR handle, a cell barcode, a unique molecular identifier (UMI), and a poly-T sequence.
Figure 5A:
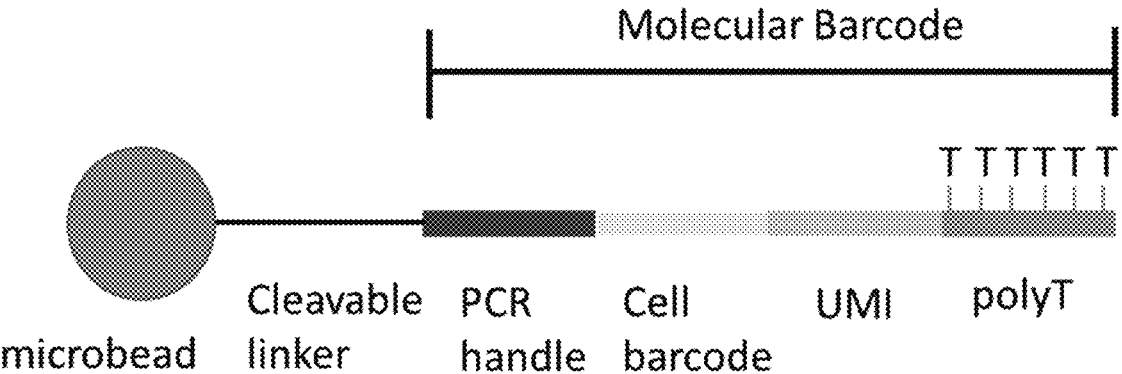
FIGS. 5A, 5B, 5C, and 5D show four non-limiting variations of the barcoded microcarrier.
Figure 5B:
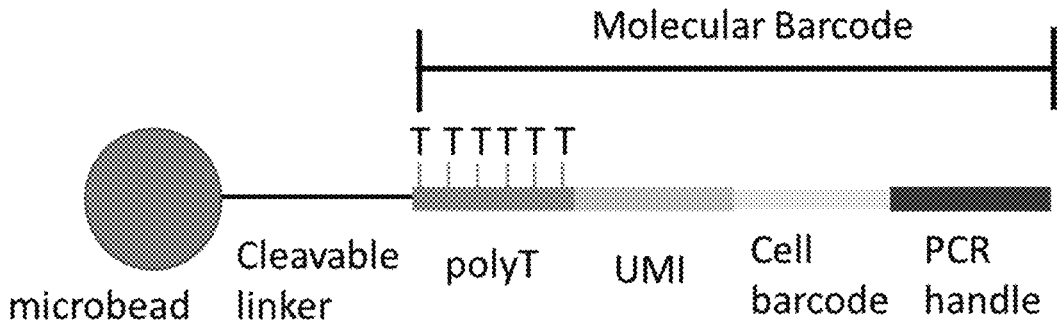
Figure 5C:
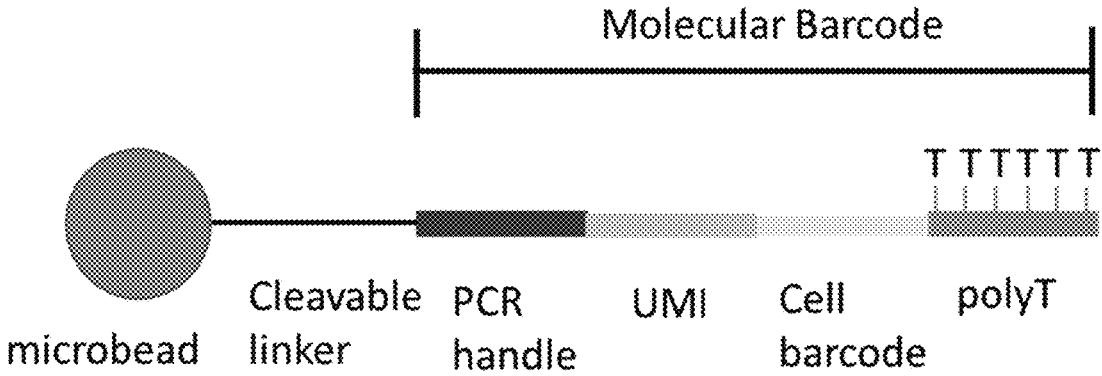
Figure 5D:
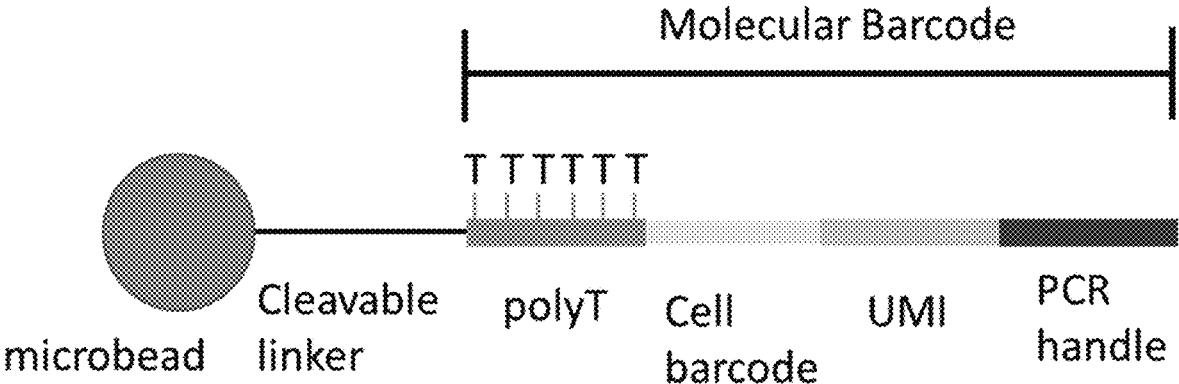

The barcoded microcarrier disclosed herein is a construct comprising a carrier bead (also known as a microbead), a plurality of cleavable linkers, and a plurality of molecular barcodes, which are linked to the microbead via their linkers. The molecular barcodes are oligonucleotides having unique sequences of nucleotides further comprising at least four sequence segments: a PCR handle, a cell barcode, a unique molecular identifier (UMI), and a poly-T sequence. The molecular barcode sequences can have more than four sequence segments for different purposes. FIG. 4 illustrates a non-limiting example of the barcoded microcarrier. The microbead is shown attached to the molecular barcode via a cleavable linker. As further shown in FIGS. 5A, 5B, 5C, and 5D, the ordering of sequences within the molecular barcode can vary in different embodiments of the invention so long as the PCR handle and poly-T sequences are located at opposite ends of the sequence. The PCR handle of the present invention is at the 5' end of the molecular barcode and the poly-T sequence is at the 3' end. The cleavable linker, therefore, can connect the oligonucleotide sequence to the bead via the PCR handle or the poly-T sequence. The molecular barcode oligonucleotide sequence has the ordering: 5'-PCR handle-cell barcode-UMI-poly-T sequence-3' or 5'-PCR handle-UMI-cell barcode-poly-T-3'. The molecular barcode can be attached to the microbead via a cleavable linker via its 3' end or its 5' end.

Microbead

The carrier bead also known as the microbead is any appropriate carrier bead for anchoring the molecular barcode via a cleavable linker that also is appropriately sized for microarray technologies. The microbead can vary in size, for example having a diameter from about 10 micrometer (μm) to about 95 μm. For example, the microbead can have a diameter of 10 μm, 15 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 95 μm, a number within any two of these values, or a range between any two of these values. In some embodiments, the microbead have a diameter of about 10 μm to about 70 μm.

The carrier beads (i.e., the microbead) can vary in material. In some embodiments, the carrier beads are made from polymers (e.g. polystyrene), metals, metal oxides, or magnetic materials, which can be optionally further coated with a polymer. In some embodiments, the beads comprise two or more types of materials. The beads of the present invention can be functionalized to attach to a linker or are functionalized with a linker using any appropriate methods.

The microbead can be dissolvable, degradable, or disruptable. The microbead can be a polymeric microbead. The microbead can be a gel bead such as a hydrogel microbead. In some embodiments, the gel bead is degradable upon application of a stimulus, including but not limited to, a thermal stimulus, a chemical stimulus, a biological stimulus, a photo-stimulus, or a combination thereof.

The microbead can be a solid bead, for example a magnetic bead. The magnetic bead can comprise a paramagnetic material coated or embedded in the magnetic bead (e.g. on a surface, in an intermediate layer, and/or mixed with other materials of the magnetic bead). The paramagnetic material refers to a material having a magnetic susceptibility slightly greater than 1 (e.g., between about 1 and about 5). A magnetic susceptibility is a measure of how much a material can become magnetized in an applied magnetic field. Paramagnetic materials include, but not limited to, magnesium, molybdenum, lithium, aluminum, nickel, tantalum, titanium, iron oxide, gold, copper, or a combination thereof.

In a plurality of barcoded microcarriers, the microbeads can be uniform in size or of heterogeneous size. In some embodiments, the microbeads in the plurality of barcoded microcarriers have an average or a median diameter of about, at least, at least about, at most, or at most about, 5 μm, 10 μm, 20 μm, 30 μm, 40 μm, 45 μm, 50 μm, 60 μm, 65 μm, 70 μm, 75 μm, 80 μm, 90 μm, or 95 μm.

In some embodiments, a microbead can be sized such that at most one microbead, not two microbeads, can fit one microwell. A size or dimension (e.g., length, width, depth, radius, or diameter) of a microbead can be different in different embodiments. In some embodiments, a size or dimension of one, or each, microbead is, is about, is at least, is at least about, is at most, or is at most about, 2 μm, 3 μm, 4 μm, 5 μm, 6 μm, 7 μm, 8 μm, 9 μm, 10 μm, 20 μm, 30 μm, 40 μm, 50 μm, 60 μm, 70 μm, 80 μm, 90 μm, 100 μm or a number or a range between any two of these values. For example, a size or dimension of one, or each, bead is about 5 μm to about 100 μm. In some embodiments, the microbead can have a dimension about 10 μm to about 70 μm. In some embodiments, the microbead can have a dimension about 30 In some embodiments, each of the plurality of microbeads has a diameter of about 10 μm to about 70 μm.

The volume of one, or each, microbead can be different in different embodiments. The volume of one, or each, microbead can be, be about, be at least, be at least about, be at most, or be at most about, 5 μm$^3$, 6 μm$^3$, 7 μm$^3$, 8 μm$^3$, 9 μm$^3$, 10 μm$^3$, 20 μm$^3$, 30 μm$^3$, 40 μm$^3$, 50 μm$^3$, 60 μm$^3$, 70 μm$^3$, 80 μm$^3$, 90 μm$^3$, 100 μm$^3$, 200 μm$^3$, 300 μm$^3$, 400 μm$^3$, 500 μm$^3$, 600 μm$^3$, 700 μm$^3$, 800 μm$^3$, 900 μm$^3$, 1000 μm$^3$, 10000 μm$^3$, 100000 μm$^3$, 1000000 μm$^3$, or a number or a range between any two of these values. The average or median volume of the microbeads in the plurality of barcoded microcarriers can be different in different embodiments. For example, the volume of one, or each, microbead can be about 1 μm$^3$ to about 1000000 μm$^3$.

Releasable Linker

The linker (e.g., cleavable/releasable linker) can be, for example, cleavable to release the molecular barcode from the microbead. The cleavable linker can be cleaved via any appropriate method or treatment, including but not limited to chemically, enzymatically, with light, including UV, visible, and near-infrared wavelengths, mechanically, and thermally. The linker can be any appropriate cleavable linker, including but not limited to, a chemical linker, including aliphatic, heteroaliphatic, aromatic, heteroaromatic, peptide or polypeptide linker, or any substitutional variants thereof, or a nucleotide or polynucleotide linker comprising sequential nucleotides. In some embodiments, the linker is or comprises a chemical linker, for example a chemical linker capable of being cleaved with light, also known as photolysis. In embodiments, the linker is or comprises a nucleotide or polynucleotide linker that can be cleaved enzymatically by a restriction enzyme.

In some embodiments, the cleavage linkers comprise a photocleavable linker. As used herein in, a photocleavable linker refers to a linker that can be cleaved from a chemical group to which it is attached to by exposure to electromagnetic radiation (e.g., UV light, visible, and near-infrared wavelengths). The wavelength of light necessary to photocleave the linker depends upon the structure and nature of the photocleavable linker used. Any photocleavable linkers known in the art can be used herein. Examples of photocleavable linkers include, but are not limited to, chemical molecules containing an o-nitrobenzyl moiety, a p-nitrobenzyl moiety, a m-nitrobenzyl moiety, a nitoindoline moiety, a bromo hydroxycoumarin moiety, a bromo hydroxyquinoline moiety, a hydroxyphenacyl moiety, a dimethozybenzoin moiety, or any combinations thereof.

In some embodiments, a releasable linker is releasably associated with the microbead, releasably linked with one of the plurality of molecular barcodes, or both. For example, when released, the releasable linker or a portion thereof can be attached to the molecular barcode, to the microbead, or both.

Molecular Barcode

The microbeads herein described are associated (e.g., attached), via a cleavable linker, to a plurality of molecular barcodes each comprising an identical cell barcode, a unique molecule identifier (UMI) different across the plurality of molecular barcodes, a PCR handle, and a poly-T sequence capable of hybridizing to poly-A tails of messenger ribonucleic acid (mRNA) targets of the plurality of fixed cells. In some embodiments, the 5' end of a molecular barcode is linked with the releasable linker. In some embodiments, the 3' end of a molecular barcode is linked with the releasable linker. The linkage between the molecular barcode and the releasable linker can be covalent or non-covalent via non-covalent bonds such as ionic bonds, hydrogen bonds, or van der Waals interactions.

The configuration of the various sequences comprised in a molecular barcode of the plurality of molecular barcodes loaded into a microwell (e.g. the cell barcode, the PCR handle, the UMI, the poly-T sequence, and/or any additional sequences) can vary depending on, for example, the particular configuration desired and/or the order in which the various components of the sequence are added as will be understood to a person skilled in the art. The molecular barcodes described herein can have the PCR handle and poly-T sequences at opposing ends of the sequence. For example, the PCR handle can be at the 5' end and the poly-T sequence at the 3' end. Either the poly-T sequence or the PCR handle can be linked to the microbead via the linker. The cell barcode and UMI need not be in a particular order so long as they are located between the opposed PCR handle and poly-T sequence. In some embodiments, the molecular barcode comprises from the 5' end to the 3' end, the PCR handle, the cell barcode, the UMI, and the poly-T sequence. In some embodiments, the molecular barcode comprises from the 5' end to the 3' end, the PCR handle, the UMI, the cell barcode, and the poly-T sequence.

Molecular barcodes can be generated from a variety of different formats, including pre-designed polynucleotide barcodes, randomly synthesized barcode sequences, microarray-based barcode synthesis, random N-mers, or combinations thereof as will be understood by a person of ordinary skill in the art.

In some embodiments, the plurality of molecular barcodes comprise, comprise about, comprise at least, comprise at least about, comprise at most, or comprise at most about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, or a number or a range between any two of these values, molecular barcodes.

A molecular barcode of the plurality of molecular barcodes can be in any suitable length, for example 4-500 nucleotides in length. In some embodiments, a molecular barcode of the plurality of molecular barcodes can be about 2 to about 500 nucleotides in length, about 2 to about 100 nucleotides in length, about 2 to about 50 nucleotides in length, about 2 to about 40 nucleotides in length, about 4 to about 20 nucleotides in length, or about 6 to 16 nucleotides in length. In some embodiments, a molecular barcode of the plurality of molecular barcodes is about, at least, at least about, at most, or at most about 2, 3, 4, 5, 6, 7, 8, 9, 10, 11, 12, 13, 14, 15, 16, 17, 18, 19, 20, 25, 30, 35, 40, 45, 50, 55, 60, 65, 70, 85, 90, 95, 100, 120, 150, 200, 250, 300, 400, or 500 nucleotides in length, or a number or a range between any two of these values.

In some embodiments, a microbead comprises, comprises about, comprises at least, comprises at least about, comprises at most, or comprises at most about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 10000000, or a number or a range between any two of these values, molecular barcodes.

PCR Handle

As used herein, a PCR handle is nucleotide sequence included for the purpose of primer attachment and PCR amplification. The PCR handle is, for example, present at the 5' end of the molecular barcode. The PCR handle can, for example, be a primer binding site or comprise a primer sequence. The primer binding sequence can be a sequencing primer sequence (or a sequencing primer binding sequence) or a PCR primer sequence (or PCR primer binding sequence). For example, the sequencing primer is a Read 1 sequence. In some embodiments, each of the plurality of molecular barcodes attached to each bead comprises the same PCR handle.

Cell Barcode

As used herein, the cell barcode is a nucleotide sequence of the molecular barcode specific to the microbead with which it is associated. In the methods disclosed herein where a single cell is isolated with the microbead, the cell barcode can be used to identify the corresponding single cell of the subsequently PCR amplified and sequenced nucleotides. The cell barcode can be any appropriate nucleotide sequence for the purposes of barcoding and identification corresponding the single cell that the cDNA originated from. For a given barcoded microcarrier, the cell barcode is an identical sequence in the plurality of molecular barcodes linked to the microbead.

The number (or percentage) of molecular barcodes attached to a microbead with cell barcodes having an identical sequence can vary. In some embodiments, the number of molecular barcodes attached to a microbead with cell barcodes having an identical sequence is, is about, is at least, is at least about, is at most, or is at most about, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, or a number or a range between any two of these values. In some embodiments, the percentage of molecular barcodes attached to a microbead with cell barcodes having an identical sequence is, is about, is at least, is at least about, is at most, or is at most about, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. For example, the cell barcodes of two (or more) molecular barcodes attached to a microbead comprise an identical sequence. In some embodiments, each of the plurality of molecular barcodes attached to a microbead comprises an identical cell barcode.

A cell barcode can be unique (or substantially unique) to a barcoded microcarrier. The number (or percentage) of barcoded microcarriers with cell barcodes having unique sequences can vary. In some embodiments, the cell barcodes of, of about, of at least, of at least about, of at most, or of at most about, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 6000000, 7000000, 8000000, 9000000, 10000000, 20000000, 30000000, 40000000, 50000000, or a number or a range between any two of these values, barcoded microcarriers can comprise different sequences. In some embodiments, the cell barcodes of, of about, of at least, of at least about, of at most, or of at most about, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values, of the barcoded microcarriers can comprise different sequences. For example, the cell barcodes of two molecular barcodes attached to two barcoded microcarriers can comprise different sequences.

The length of a cell barcode of a barcoded microcarrier (or each cell barcode of a barcoded microcarrier or all cell barcodes of all barcoded microcarriers) can vary. In some embodiments, a cell barcode of a barcoded microcarrier (or each cell barcode of a barcoded microcarrier or all cell barcodes of all barcoded microcarriers) is, is about, is at least, is at least about, is at most, or is at most about, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or a number or a range between any two of these values, nucleotides in length. For example, a cell barcode can be at least 6 nucleotides in length.

The number of unique cell barcode sequences in the plurality of barcoded microcarriers can vary. In some embodiments, the number of unique cell barcode sequences in the plurality of barcoded microcarriers is, is about, is at least, is at least about, is at most, or is at most about, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 6000000, 7000000, 8000000, 9000000, 10000000, 20000000, 30000000, 40000000, 50000000, or a number or a range between any two of these values.

Unique Molecular Identifier

As used herein, the unique molecular identifier (UMI) is a nucleotide sequence of the molecular barcode that is used as a molecular tag to detect and quantify different mRNA transcripts. The UMI is specific to the mRNA sequence to which the molecular barcode binds via its poly-T sequence. In the methods of the present invention, the UMI can be used to identify the mRNA strand to which a given molecular barcode binds, following subsequent analysis such as sequencing.

The number (or percentage) of UMIs of molecular barcodes attached to a microbead with different sequences can vary. For example, the number of UMIs of molecular barcodes attached to a microbead with different sequences can be, be about, be at least, be at least about, be at most, or be at most about, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 6000000, 7000000, 8000000, 9000000, 10000000, 20000000, 30000000, 40000000, 50000000, or a number or a range between any two of these value. In some embodiments, the percentage of UMIs of molecular barcodes attached to a microbead with different sequences is, is about, is at least, is at least about, is at most, or is at most about, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. For example, the UMIs of two molecular barcodes attached to a microbead of the plurality of microbeads can comprise different sequences.

The number of molecular barcodes attached to a microbead with UMIs having a particular sequence (or an identical sequence) can vary. In some embodiments, the number of molecular barcodes attached to a microbead with UMIs having a particular sequence (or an identical sequence) is, is about, is at least, is at least about, is at most, or is at most about, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, or a number or a range between any two of these values. For example, the UMIs of two molecular barcodes attached to a microbead can comprise a particular sequence (or an identical sequence).

Molecular barcodes attached to different microbeads can have UMIs with a particular sequence (or an identical sequence). In some embodiments, the number of microbeads attached thereto molecular barcodes having UMIs with a particular sequence (or an identical sequence) is, is about, is at least, is at least about, is at most, or is at most about, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 6000000, 7000000, 8000000, 9000000, 10000000, 20000000, 30000000, 40000000, 50000000, or a number or a range between any two of these values. For example, the UMIs of two molecular barcodes attached to two microbeads of the microbeads can comprise an identical sequence.

The length of a UMI of a barcoded microcarrier (or each UMI of a barcoded microcarrier or all UMIs of all barcoded microcarriers) can vary. For example, a UMI of a barcoded microcarrier (or each UMI of a barcoded microcarrier or all UMIs of all barcoded microcarriers) is, is about, is at least, is at least about, is at most, or is at most about, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or a number or a range between any two of these values, nucleotides in length. In some embodiments, a UMI can be at least 6 nucleotides in length.

The number of unique UMI sequences of a barcoded microcarrier can vary. For example, the number of unique UMI sequences is, is about, is at least, is at least about, is at most, or is at most about, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 6000000, 7000000, 8000000, 9000000, 10000000, 20000000, 30000000, 40000000, 50000000, or a number or a range between any two of these value.

Poly-T Sequence

The poly-T sequence is a nucleotide sequence comprising sequential thymine nucleotides for annealing to mRNA nucleotides of the cell by hybridizing to poly-A tails of mRNA nucleotides. In the methods of the present invention, the poly-T sequence is at the 3' end of the molecular barcode and anneals the molecular barcode oligonucleotide sequence to the mRNA nucleotides of the cell after the cleavable linker has been cleaved. The poly-T sequences used herein generally have about 3 to about 50 repeating thymine nucleotides, for example, about 10 to about 35 repeating thymine nucleotides, and about 16 to about 30 repeating thymine nucleotides.

In some embodiments, the poly-dT of the molecular barcodes attached to a barcoded microcarrier can be identical (e.g., same number of dT). In some embodiments, the poly-dT of the molecular barcodes attached to a barcoded microcarrier can be different (e.g., different number of dT). The percentage of the molecular barcodes of the plurality of molecular barcodes attached to a barcoded microcarrier with an identical poly-dT sequence can vary. In some embodiments, the percentage of the molecular barcodes of the plurality of molecular barcodes attached to a barcoded microcarrier with an identical poly-dT sequence is, is about, is at least, is at least about, is at most, is at most about, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.9%, 100%, or a number or a range between any two of these values.

The length of a poly-dT sequence can vary. In some embodiments, a poly-dT sequence is, is about, is at least, is at least about, is at most, or is at most about, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or a number or a range between any two of these values, nucleotides in length. For example, a poly-dT sequence is at least 10 nucleotides in length.

Nucleic Acid Targets and Cells

The plurality of fixed cells for loading into a plurality of microwells according to the methods and systems described herein can be obtained from any organism of interest such as Monera (bacteria), Protista, Fungi, Plantae, and Animalia Kingdoms. For example, the plurality of fixed cells can comprise eukaryotic cells, prokaryotic cells, cells infected with a virus, or a combination thereof. In some embodiments, a cell of the plurality of fixed cells can be a mammalian cell, and particularly a human cell such as T cells, B cells, natural killer cells, stem cells, cancer cells, or cells infected with a virus. In some embodiments, the cell can be an immune cell. For example, the cell can be a neutrophil, an eosinophil, a basophil, a mast cell, a monocyte, a macrophage, a dendritic cell, a natural killer cell, a lymphocyte, a B cell, a T cell, or a combination thereof. The plurality of fixed cells can be of a same kind or of different kinds.

In some embodiments, the cell is a cancer cell. The nucleic acid target can be a cancer gene (or a disease-related gene), or an RNA (e.g., mRNA) product thereof. The methods herein described can thus determine a profile (e.g., RNA expression profile) of a cancer gene (or a disease-related gene), mutations of the gene, and abundances of the mutations.

In some embodiments, the cell is infected with a virus. The nucleic acid target can be a gene of the virus, or a nucleic acid product (e.g., RNA) thereof. The virus can be an RNA virus. The nucleic acid target can comprise an RNA of the gene of the virus. The method described herein can thus determine a profile (e.g., an RNA expression profile) of the cell and a nucleic acid profile (e.g., RNA expression profile) of the virus.

In some embodiments, an expression profile comprises an absolute abundance of the mRNA targets, a relative abundance of the mRNA targets, or both. An abundance can be a number or a frequency of occurrences. In some embodiments, the absolute abundance of the molecules of a nucleic acid target can comprise a number of occurrences of the molecules of the nucleic acid target. In some embodiments, the relative abundance of the molecules of a nucleic acid target can comprise a number of occurrences of the molecules of the nucleic acid target relative to a number of occurrences of the molecules of a total nucleic acid targets or relative to a number of occurrences of the molecules of another nucleic acid target that is different from the nucleic acid target.

The number of different nucleic acid targets (e.g. mRNAs of different genes or mRNAs of different sequences) the molecular barcodes are capable of binding can be different in different embodiments. In some embodiments, the number of different nucleic acid targets the molecular barcodes attached to a microbead (or each microbead) are capable of binding is, is about, is at least, is at least about, is at most, or is at most about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 1000, 2000, 3000, 4000, 5000, 6000, 7000, 8000, 9000, 10000, 50000, 100000, 1000000, 5000000, or a number or a range between any two of these values. One molecular barcode attached to a microbead (or each microbead) can bind to a molecule (or a copy) of a nucleic acid target. Molecular barcodes attached to a microbead (or each microbead) can bind to molecules (or copies) of a nucleic acid target.

In some embodiments, the plurality of fixed cells can be diluted prior to loading to ensure majority of the microwells comprise at most one cell with low doublets (more than one cell in one microwell). A dilution can be prepared such that a desired cell concentration is achieved. The cell concentration can be between $1 \times 10^4$ and $1 \times 10^6$ (e.g., about, at least, at least about, at most, at most about, $1 \times 10^4$, $2 \times 10^4$, $3 \times 10^4$, $4 \times 10^4$, $5 \times 10^4$, $6 \times 10^4$, $7 \times 10^4$, $8 \times 10^4$, $9 \times 10^4$, $1 \times 10^5$, $1.5 \times 10^5$, $2 \times 10^5$, $2.5 \times 10^5$, $3 \times 10^5$, $3.5 \times 10^5$, $4 \times 10^5$, $4.5 \times 10^5$, $5 \times 10^5$, $5.5 \times 10^5$, $6 \times 10^5$, $6.5 \times 10^5$, $7 \times 10^5$, $7.5 \times 10^5$, $8 \times 10^5$, $8.5 \times 10^5$, $9 \times 10^5$, $1 \times 10^6$, or a number or a range between any two of these values) cells/mL. In some embodiments, the cell concentration is about $1 \times 10^5 - 3 \times 10^5$ (e.g., about, at least, at least about, at most, at most about, $1 \times 10^5$, $1.1 \times 10^5$, $1.2 \times 10^5$, $1.3 \times 10^5$, $1.4 \times 10^5$, $1.5 \times 10^5$, $1.6 \times 10^5$, $1.7 \times 10^5$, $1.8 \times 10^5$, $1.9 \times 10^5$, $2.0 \times 10^5$, $2.1 \times 10^5$, $2.2 \times 10^5$, $2.3 \times 10^5$, $2.4 \times 10^5$, $2.5 \times 10^5$, $2.6 \times 10^5$, $2.7 \times 10^5$, $2.8 \times 10^5$, $2.9 \times 10^5$, $3.0 \times 10^5$, or a number or a range between any two of these values).

Cells described herein can be obtained from a cell sample. A cell sample comprising cells can be obtained from any source including a clinical sample and a derivative thereof, a biological sample and a derivative thereof, a forensic sample and a derivative thereof, an environmental sample and a derivative thereof, and a combination thereof. A cell sample can be collected from any bodily fluids including, but not limited to, blood, urine, serum, lymph, saliva, anal, and vaginal secretions, perspiration and semen of any organism. A cell sample can be products of experimental manipulation including purification, cell culturation, cell isolation, cell separation, cell quantification, cell sorting, sample dilution, or any other cell sample processing approaches. A cell sample can be obtained by dissociation of any biopsy tissues of any organism including, but not limited to, skin, bone, hair, brain, liver, heart, kidney, spleen, pancreas, stomach, intestine, bladder, lung, and esophagus.

Loading Microwells

The methods, systems, and composition herein described involve the use of microwells, for example microwells in microwell arrays. The term "microwell," as used herein, refers to a well with a volume of less than 1 mL. A microwell array can contain a number of microwells arranged in rows and columns. The size and spacing of the microwells may vary depending on different applications. A microwell can contain one particle or two or more particles of the same type or different types.

The microwell array comprising a plurality of microwells can be formed from any suitable material as will be understood by a person skilled in the art. For example, a microwell array comprising a plurality of microwells can be formed from a material selected from the group consisting of silicon, glass, ceramic, elastomers such as polydimethylsiloxane (PDMS), thermoset polyester, thermoplastic polymers such as polystyrene, polycarbonate, poly(methyl methacrylate) (PMMA), poly-ethylene glycol diacrylate (PEGDA), teflons, polyurethane (PU), paper, hydrogels, composite materials such as cyclic-olefin copolymer, or combinations thereof.

In some embodiments, the microwell array can comprise an inlet port in fluid communication with the plurality of microwells. The microwell array can also comprise an outlet port in fluid communication with the plurality of microwells. Microwells can be introduced with samples, free reagents, and/or reagents encapsulated in microcapsules. The reagents can comprise restriction enzymes, ligase, polymerase, fluorophores, oligonucleotide barcodes, oligonucleotide probes, adapters, buffers, dNTPs, ddNTPs, and other reagents required for performing the methods described herein. Samples and reagents can be perfused from the inlet port through a flow channel to deliver to the microwell array, and the waste can be pushed out from the outlet port and removed.

In some embodiment, the microwell array can be operated in an open well condition. There is no enclosed flow channel on the top of the microwell array. Reagents can be freely exchanged by directly adding to and removing from the surface of the microwell array. Microwells can be introduced with samples, free reagents, and/or reagents encapsulated in microcapsules. The reagents can comprise restriction enzymes, ligase, polymerase, fluorophores, oligonucleotide barcodes, oligonucleotide probes, adapters, buffers, dNTPs, ddNTPs, and other reagents required for performing the methods described herein.

A microwell can be sized so that it can fit at most one microbead (and one cell), not two microbeads. A size or dimension (e.g., length, width, depth, radius, or diameter) of a microwell can be different in different embodiments. In some embodiments, a size or dimension of one, one or more, or each, of the plurality of microwells is, is about, is at least, is at least about, is at most, or is at most about, 2 micrometer (μm), 3 μm, 4 μm, 5 μm, 6 μm, 7 μm, 8 μm, 9 μm, 10 μm, 20 μm, 30 μm, 40 μm, 50 μm, 60 μm, 70 μm, 80 μm, 90 μm, 100 μm, 110 μm, 120 μm, 130 μm, 140 μm, 150 μm, 160 μm, 170 μm, 180 μm, 190 μm, 200 μm, 210 μm, 220 μm, 230 μm, 240 μm, 250 μm, 260 μm, 270 μm, 280 μm, 290 μm, 300 μm, or a number or a range between any two of these values. For example, a size or dimension of one, one or more, or each, of the plurality of microwells is about 5 μm to about 100 μm. In some embodiments, each of the plurality of microwells has a diameter (width) of about 10 μm to about 100 μm. In some embodiments, the microwells of the plurality of microwells have an average or a median diameter (width) of about 10 μm to about 100 μm.

The volume of one, one or more, or each, of the plurality of microwells can be different in different embodiments. The volume of one, one or more, or each, of the plurality of microwells can be, be about, be at least, be at least about, be at most, or be at most about, 5 μm³, 6 μm³, 7 μm³, 8 μm³, 9 μm³, 10 μm³, 20 μm³, 30 μm³, 40 μm³, 50 μm³, 60 μm³, 70 μm³, 80 μm³, 90 μm³, 100 μm³, 200 μm³, 300 μm³, 400 μm³, 500 μm³, 600 μm³, 700 μm³, 800 μm³, 900 μm³, 1000 μm³, 10000 μm³, 100000 μm³, 1000000 μm³, or a number or a range between any two of these values. For example, the volume of one, one or more, or each, of the plurality of microwells is about 5 μm³ to about 1000000 μm³.

The number of microwells in a microwell array can vary. In some embodiments, the number of microwells is, is about, is at least, is at least about, is at most, or is at most, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, or a number or a range between any two of these values. For example, the number of microwells can be at least 1000 microwells. In some embodiments, the plurality of microwells comprises about 1,000 microwells to about 500,000 microwells.

The percentage of the plurality of microwells comprising a single cell and a single barcoded microcarrier can vary. In some embodiments, the percentage of the plurality of microwells comprising a single cell and a single barcoded microcarrier is, is about, is at least, is at least about, is at most, or is at most about, 5%, 8%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or a number or a range between any two of these values. For example, at least 50% of microwells of the plurality of microwells can comprise a single cell of the plurality of fixed cells and a single barcoded microcarrier of the plurality of barcoded microcarriers. In some embodiments, at least 5%, at least 10%, at least 15%, at least 25%, at least 50%, or at least 75% of the plurality of microwells each is loaded with one of the plurality of fixed cells and one of the plurality of barcoded microcarriers. In some embodiments, at least 80% of the plurality of microwells each is loaded with one of the plurality of fixed cells and one of the plurality of barcoded microcarriers. In some embodiments, at least 90% of the plurality of microwells each is loaded with one of the plurality of fixed cells and one of the plurality of barcoded microcarriers.

The percentage of the plurality of microwells comprising no cell, or two or more cells, of the plurality of fixed cells can vary. In some embodiments, the percentage of the plurality of microwells comprising no cell or two or more cells of the plurality of fixed cells is, is about, is at least, is at least about, is at most, or is at most about, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 60%, 70%, 80%, 90%, 95%, or a number or a range between any two of these values. For example, at most 10% of microwells of the plurality of microwells can comprise two or more cells of the plurality of fixed cells. As another example, at most 95% of microwells of the plurality of microwells can comprise no cell of the plurality of fixed cells.

The percentage of the plurality of microwells comprising no barcoded microcarrier or two or more barcode microcarriers of the plurality of barcode microcarriers can vary. In some embodiments, the percentage of the plurality of microwells comprising no barcode microcarrier or two or more barcode microcarriers of the plurality of barcode microcarriers is, is about, is at least, is at least about, is at most, or is at most about, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, or a number or a range between any two of these values. For example, at most 10% of microwells of the plurality of microwells can comprise two or more barcode microcarriers of the plurality of barcode microcarriers. For example, at most 10% of microwells of the plurality of microwells can comprise no barcode microcarrier of the plurality of barcode microcarriers.

The total number of barcoded microcarriers loaded into the plurality of microwells can vary. In some embodiments, the number of barcoded microcarriers loaded into a plurality of microwells is, is about, is at least, is at least about, is at most, or is at most, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 6000000, 7000000, 8000000, 9000000, 10000000, 20000000, 30000000, 40000000, 50000000, or a number or a range between any two of these values. For example, the number of barcoded microcarriers loaded into a plurality of microwells can be at least 80,000 barcoded microcarriers.

In some embodiments, barcoded microcarriers are loaded to the microwells such that the percentage of microwells each loaded with one barcoded microcarrier is, is about, is at least, is at least about, is at most, or is at most about, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or a number or a range between any two of these values. For example, at least 80% of the plurality of microwells can be each loaded with one barcoded microcarrier. In some embodiments, at least 90% of the plurality of microwells can be each loaded with one barcoded microcarrier.

Methods and Systems

Provided herein are high throughput single-cell mRNA profiling methods and systems for fixed biological samples. The methods, in some embodiments, comprise loading permeabilized fixed cells (e.g., in a solution, such as phosphate buffered saline, i.e. "PBS"), barcoded microcarriers, and a reverse transcription mixer for mRNA reverse transcription into a microwell array.

The method, in some embodiments, comprises high throughput single-cell mRNA profiling methods using a microfluidic device with a microwell array, where single cells are isolated along with a barcoded microcarrier comprising a microbead and a plurality of molecular barcodes attached to the microbead via cleavable linkers. The molecular barcodes, also called "unique oligonucleotide sequences" can be released from the beads and allowed to diffuse into the cells to capture or barcode the mRNAs of the cells. A reverse transcription reaction can be performed to convert the barcoded mRNAs to barcoded cDNAs. The cells can be lysed or digested to release the barcoded cDNAs which can be sequenced.

Figure 6A:
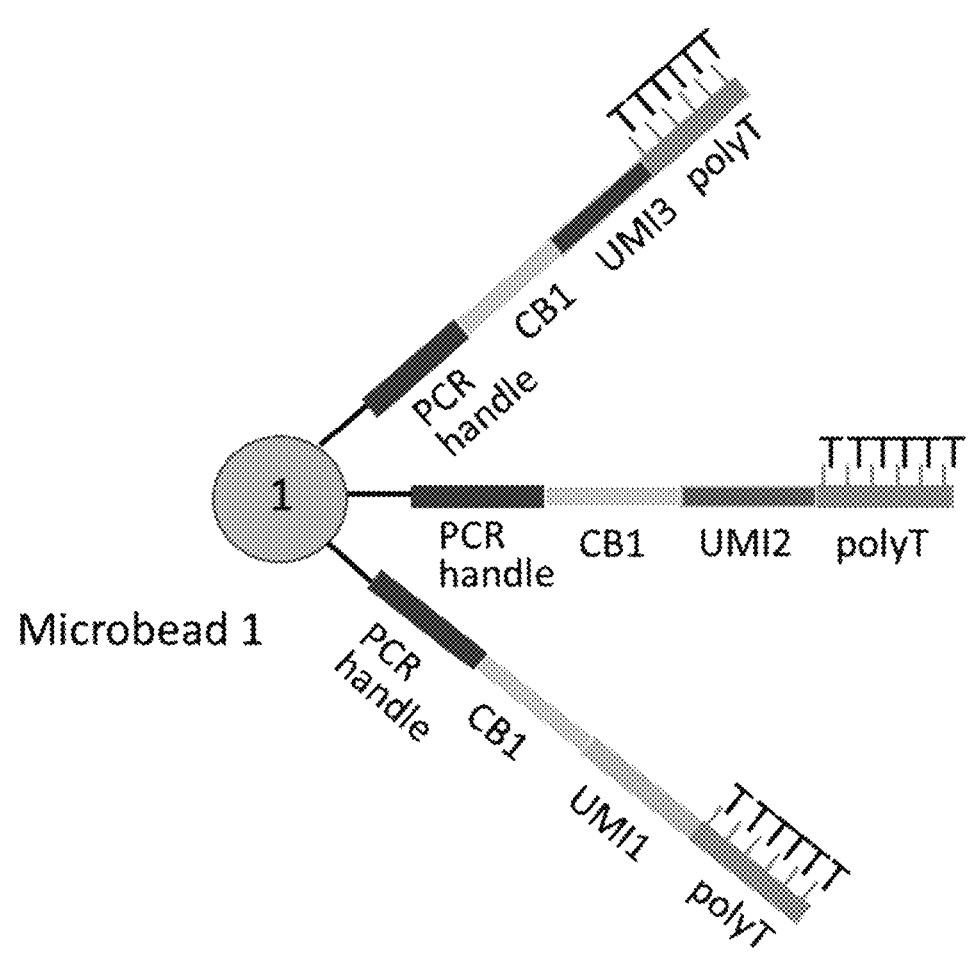
FIGS. 6A and 6B show non-limiting representations of two simplified barcoded microcarriers suitable for use in the methods, compositions and kits disclosed herein. In these representative schematics, for simplicity, only three unique oligonucleotide sequences are shown. The method allows for a cell-specific cell barcode (abbreviated "CB1" and "CB2") and unique molecular identifiers (abbreviated "UMI1", "UMI2", and "UMI3") that identify both the cell and mRNA polynucleotide or cDNA reverse-transcribed therefrom in a subsequent PCR amplification and sequencing. Shown is a cell barcode "CB1" specific for a first cell, i.e. cell 1 and three different UMIs ("UMI1", "UMI2", and "UMI3") for binding to the mRNAs of that cell (FIG. 6A), and a cell barcode "CB2" specific for a second cell, i.e. cell 2 and three different UMIs ("UMI1", "UMI2", and "UMI3") for binding to the mRNAs of that cell (FIG. 6B).
Figure 6B:
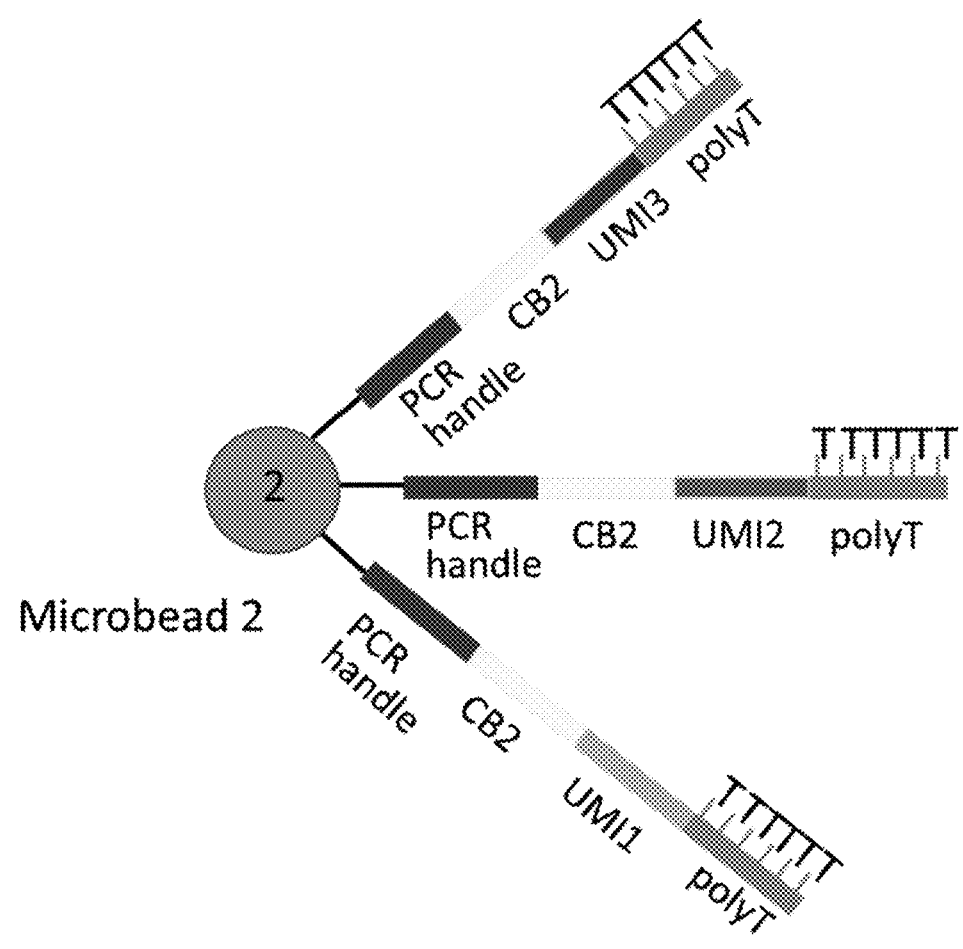

As shown in FIGS. 6A and 6B, the mRNA sequences and cDNA generated therefrom can be identified by two nucleotide sequence segments: the cell barcode (abbreviated CB1 or CB2 in the figures) and the UMI. The cell barcode is specific to the cell, or bead, present in the microwell. Microbead 1 shown in FIG. 6A has the cell barcode "CB1" whereas microbead 2 shown in FIG. 6B has the cell barcode "CB2". Each barcoded microcarrier comprises a plurality of linkers and a plurality of molecular barcodes. For a given barcoded microcarrier, the cell barcode in each of the plurality of cleavable oligonucleotide sequences is identical, as shown with the "CB1" and "CB2" notation, whereas the UMI is different for each of the plurality of molecular barcodes. In this manner, each mRNA sequence in the same single cell binding to one of the unique oligonucleotide sequences is identified with a unique UMI. It can be appreciated that the set of UMI sequences used in each microcarrier can be either identical or different.

Barcoded microcarriers can be microbeads, e.g., polymeric beads. The barcoded microcarriers are considered barcoded because that they have a plurality of molecular barcodes, or oligonucleotides, wherein each oligonucleotide comprises a unique sequence of nucleotides, linked to the surface of microcarriers. As shown in FIG. 4, the oligonucleotide having a unique sequence of nucleotides has at least four segments: a sequence segment with multiple oligo(dT) (polyT) for capturing the mRNA; a sequence segment for labeling the microcarrier, also called the cell barcode, wherein the labeling sequence segment is identical for the same microcarrier whereas it is different for different microcarriers; a sequence segment for uniquely identifying different captured mRNA, also called UMI; and a sequence segment such as a PCR handle for PCR amplification. Once cleaved from the microcarrier the polyT sequence segment is exposed to capture the polyA tail of the cell RNA. Non-limiting orders of the microbeads and various components of the molecular barcodes on the barcoded microcarrier include:

(1) bead, linker, PCR handle, cell barcode, UMI, and poly T;

(2) bead, linker, PCR handle, UMI, cell barcode, and poly T;

(3) bead, linker, polyT, UMI, cell barcode, and PCR handle;

(4) bead, linker, polyT, cell barcode, UMI, and PCR handle.

The linkages of the oligonucleotides or molecular barcodes to the microcarriers can be cleavable. The cleavable linker can be a cleavable chemical moiety or a cleavable nucleotide sequence with unique sequence which can be recognized by restriction enzymes. The cleavable linker can be cleaved via any appropriate method or treatment, including but not limited to chemically, enzymatically, with light, including UV, visible, and near-infrared wavelengths, mechanically, and thermally. The barcoded microcarrier beads, in some embodiments, have a diameter of about 10 μm to about 70 μm.

A microwell array of the present disclosure, in some embodiments, comprises from about 1,000 microwells to about 500,000 microwells. The microwells can be circular, square, rectangular, triangular, or honeycomb. Other microwell shapes, chambers, and channels are encompassed herein. In some embodiments, the microwell array comprises microwells having a diameter (width) from about 10 μm to about 100 μm.

The methods and systems provided herein, in some embodiments, are high throughput, for example from about 100 cells to about 50,000 cells with the same or different cell types can be processed at the same time. In some embodiments, from about 10,000 to about 20,000 cells are loaded onto the microwell array.

The methods provided herein can be used to investigate different cell types and is not limited to a particular cell type.

In some embodiments, the microwell array is loaded with cells to achieve a well occupancy rate of about 5% to about 15%. This level of loading helps to minimize the number of microwells having two or more cells. In other words, this loading level helps to ensure that those microwells contain only a single cell.

In some embodiments, greater than about 80% of the microwells of the array comprise a single barcoded microcarrier. In some embodiments, greater than about 90% of the microwells of the array comprise a single barcoded microcarrier. These levels of loading of the barcoded microcarrier help ensure that most microwells contain a barcoded microcarrier.

Therefore, the combination of about 5% to about 15% cell loading coupled with greater than about 80% or great than about 90% barcoded microcarrier loading helps to ensure that most of the microwells contain a single cell also contain a single barcoded microcarrier.

Figure 2A:
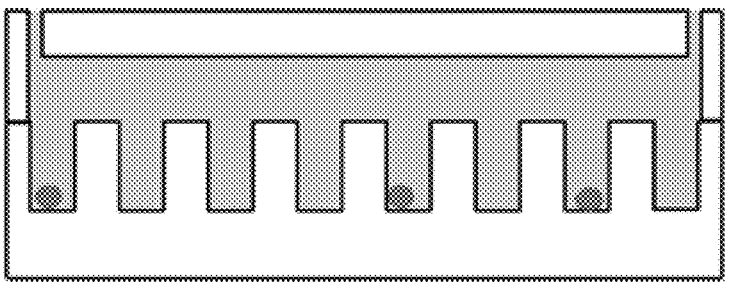
FIGS. 2A, 2B, and 2C illustrate the separation of single cells and barcoded microcarriers in MX-CDB scRNA-seq. Step 1 (FIG. 2A): A cell suspension is loaded into a microwell array to separate the cells into single cells. Step 2 (FIG. 2B): The barcoded microcarriers, i.e. the barcoded microbeads, are loaded into the microwell array to achieve a >80% microwell occupancy of the microwells with a microcarrier. Step 3 (FIG. 2C): The microwell array is sealed with a cover, which can include an oil layer, to provide microwells having a single cell and one barcoded microcarrier isolated in a microwell.
Figure 2B:
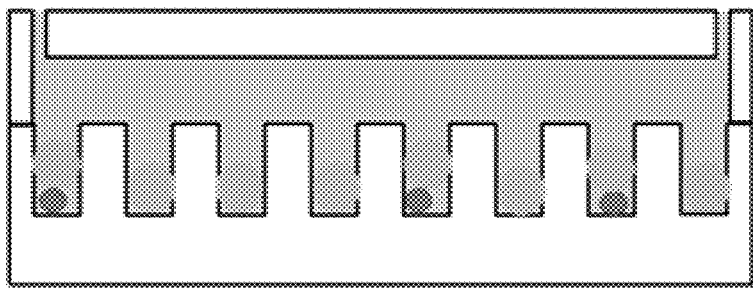
Figure 2C:
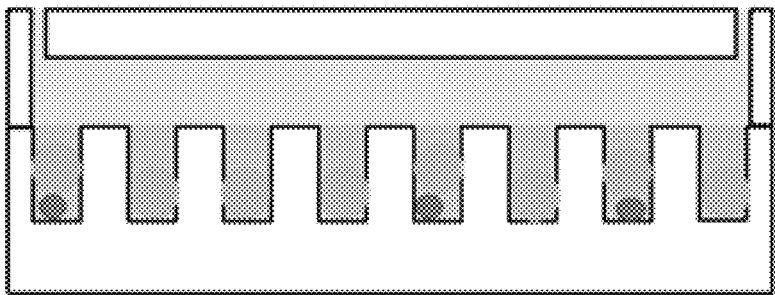

As shown in FIGS. 2A, 2B, and 2C for the MX-CDB scRNA-seq methods and system, the materials are loaded into the microwells. First, a cell suspension is loaded into a microwell array to separate the cells into single cells as shown in FIG. 2A. Next, the barcoded microbeads are loaded into the microwell array to achieve a >80%, or alternatively a >90% microwell occupancy of the microwells with a microbead, as shown in FIG. 2B. The microwell array is then sealed with a cover, which can include an oil layer, or a glass layer, or a polymer layer, to provide some microwells containing both a single cell and one microbead isolated within a microwell, as shown in FIG. 2C.

The methods of the present disclosure, in some embodiments, optionally comprise sealing the microwell array with a cover to generate a sealed microwell array comprising the permeabilized fixed cells, barcoded microcarriers, and reverse transcription mixer. The cover can be a physical structure, including but not limited to a physical structure comprising or being a film, a membrane, a glass slide, or a combination thereof. Non-limiting examples of the physical structure include a single or double-layer of PDMS film or a glass slide (with or without a manual clamp). The physical structure can be permeable, semi-permeable or not permeable. In some embodiments, the physical structure is a nanoporus membrane. In some embodiments, the microwells or the microwell array is not sealed with a nanoporous membrane. The cover can be a fluid barrier. For example, the cover can be an oil to separate and seal the aqueous mixture of cells, microcarriers, and reaction solution. An oil can be utilized if it is chosen to be denser than the aqueous phase of the cell sample such that it can push away all aqueous solution and seal the microwells. But due to surface tension and microdimension of the microwells, the oil cannot flow into the microwells. In some embodiments, the oil is fluorinated hydrocarbon oil.

Figure 3A:
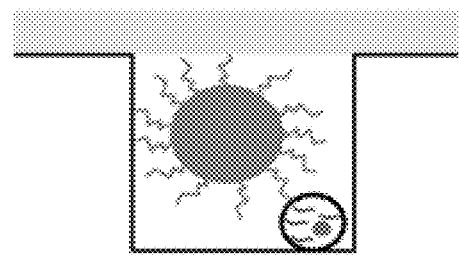
FIGS. 3A, 3B, and 3C illustrate further steps of the MX-CDB workflow. First, a single cell and one microbead are separated and sealed in an individual microwell (FIG. 3A). The molecular barcodes are cleaved from the microbeads and allowed to diffuse into the fixed and permeabilized cells to bind with mRNAs of the cells. Next in-cell reverse transcription is performed to generate barcoded cDNAs (FIG. 3B). The cells are then lysed or digested to release the barcoded cDNAs, for further sequencing (FIG. 3C).
Figure 3B:
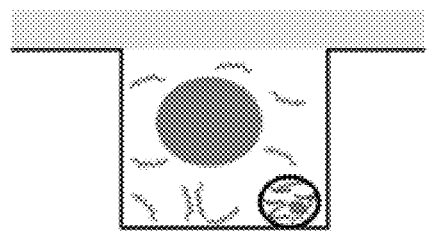
Figure 3C:
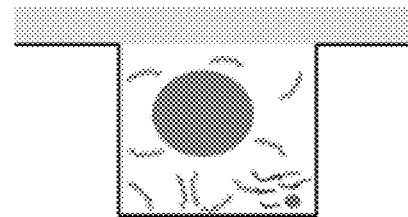

FIGS. 3A, 3B, and 3C show some steps of the methods and system disclosed herein. Once a single cell and one microbead are sealed in an individual microwell (FIG. 3A, also see FIG. 2C), the barcodes are cleaved from the microbeads and allowed to diffuse into the fixed and permeabilized cells to bind with mRNAs of the cells. Next in-cell reverse transcription is performed to generate barcoded cDNAs (FIB. 3B). The cells are then lysed or digested to release the barcoded cDNAs, for further sequencing (FIG. 3C).

The cleavage step, in some embodiments, comprises exposing the sealed microwell array with a mixture of cells, microcarriers, and reaction solution under UV light to photo cleave the linkage, i.e., photolysis, of the oligonucleotides to the microbeads (e.g., irradiated with near-UV light, 300-350 nm wavelength, for about 5 minutes or more as appropriate). In another embodiment, the cleavage step comprises using enzymes to digest the linkage of oligonucleotides to the microcarriers (e.g., restriction enzymes to digest specific sequence in the linkage of oligonucleotides to the microcarriers).

Following the cleavage step, the microfluidic device can be incubated for a period of time (e.g., from about 30-90 minutes) to allow the released oligonucleotides to diffuse into the permeabilized fixed cells to bind to the cellular mRNAs. For example, the polyT sequence of the oligonucleotides released from the microcarriers will bind to the polyA tail of the mRNAs of the cells. In some embodiments, increased temperature can be used to facilitate the diffusion and binding (e.g., from about 40-50° C.).

In some embodiments, the methods further comprise using a reverse transcription process to reverse transcribe the mRNAs that was captured by the oligonucleotides to the cDNAs.

In some embodiments, the methods further comprise lysing or digesting the fixed cells with cell lysis or digestion buffer to release the cDNAs generated in the reverse transcription process. The lysis or digestion buffer can comprise detergents, salts, or enzymes, or mixtures thereof.

In some embodiments, the methods further comprise collecting the generated cDNAs from the microfluidic device (e.g., collecting the liquid from the microfluidic device wherein the liquid contains the cDNAs generated by reverse transcription).

In some embodiments, the collected cDNAs are amplified through polymerase chain reaction (PCR) and purified before library preparation for sequencing. The prepared cDNA segments are then sequenced using any appropriate sequencing method known in the art.

In some embodiments, single-cell mRNA quantification is used to determine the absolute abundance of RNA nucleotides in a single cell. In another aspect, the relative abundance of RNA nucleotides in multiple cells can be quantified. These quantities may be used for RNA profiling or transcriptomics for the purposes of transcriptome analysis in any suitable cell sample.

One or more steps of the methods and systems disclosed herein are further described in the following sections.

Cell Fixation and Permeabilization

Methods for fixing a plurality of cells to generate a plurality of fixed cells are disclosed herein. The term "fix" or "fixation" as used herein refers to the process of preserving biological materials such as tissues, cells, organelles, and molecules from decay and/or degradation. Fixation can be accomplished using any conventional protocols known in the art. In some embodiments, fixation can be a chemical fixation using a fixation reagent (e.g., a reagent that contains at least one fixative).

The method disclosed herein can comprise contacting a plurality of cells with a fixation agent. Cells can be contacted by a fixation reagent for a suitable time period which can vary because of, for example the temperature, the nature of the sample, and on the choice of fixatives. For example, a cell sample can be contacted by a fixation reagent for about, at least, at least about, at most, at most about 24 hours, 18 hours, 12 hours, 8 hours, 6 hours, 4 hours, 2 hours, 60 minutes, 45 minutes, 30 minutes, 25 minutes, 20 minutes, 15 minutes, 10 minutes, 5 minutes, or 2 minutes, or a number or a range between any two of these values.

Cells can be contacted by a fixation reagent at various temperatures, depending on the protocol and the reagent used. For example, in some embodiments a cell sample can be contacted by a fixation reagent at a temperature ranging from −22° C. to 55° C., where specific ranges of interest include, but are not limited to: 50 to 54° C., 40 to 44° C., 35 to 39° C., 28 to 32° C., 20 to 26° C., 0 to 6° C., and −18 to −22° C. In some embodiments, a cell sample can be contacted by a fixation reagent at a temperature of −20° C., 4° C., room temperature (e.g., 22-25° C.), 30° C., 37° C., 42° C., or 52° C.

Non-limiting examples of fixation reagents include cross-linking fixatives, precipitating fixatives, oxidizing fixatives, Hepes-glutamic acid buffer-mediated organic solvent protection effect (HOPE) fixatives, or a combination thereof. A fixation reagent can contain more than one fixative. Cross-linking fixatives chemically join two or more molecules by a covalent bond and a wide range of cross-linking reagents known in the art can be used. Examples of suitable cross-liking fixatives include but are not limited to aldehydes (e.g., formaldehyde, also commonly referred to as "formalin"; paraformaldehyde, the polymeric form of formaldehyde; and glutaraldehyde), imidoesters, NHS (N-Hydroxysuccinimide) esters, and the like. Examples of suitable precipitating fixatives include but are not limited to alcohols (e.g., methanol, ethanol, etc.), acetone, acetic acid, etc. In some embodiments, the fixative is formaldehyde (i.e., paraformaldehyde or formalin). A suitable final concentration of formaldehyde in a fixation reagent is 0.1 to 10%, such as 1-8%, 1-4%, 1-2%, 3-5%, or 3.5-4.5%. In some embodiments, a cell sample comprising a plurality of cells is fixed in a final concentration of 4% paraformaldehyde. In some embodiments, the cell sample is contacted with a fixation reagent containing formaldehyde, paraformaldehyde, glutaraldehyde, or a combination thereof. In some embodiments, the cells are contacted with glycerol, acetic acid, N-acetyl cysteine (NAC) and methanol, for example the cells are contacted with glycerol, acetic acid and NAC first, then followed by methanol treatment.

The method comprises herein can further comprise permeabilizing cells. The fixation of cells and permeabilizing the cells can be performed in one step or in separate steps. In some embodiments, the plurality of fixed cells comprises permeabilized cells. The term "permeabilize" as used herein refers to the process of rendering cells (e.g. cell membrane) permeable to reagents such as chemical substrates, enzymes, oligonucleotides such that the reagents (e.g., molecular barcodes) can pass through the lipid bilayer membrane of the cell. The term "permeable" can be a relative term to indicate permeability to specific reagents (e.g., of a particular size) with respect to other reagents. Accordingly, in some embodiments, permeabilized cells are permeable to certain reagents but not to others. In some embodiments, permeability of the permeabilized cells are higher for nucleic acid molecules (e.g., molecular barcodes) than one or more types of macromolecules (e.g., proteins).

Permeabilized cells can be generated by, for example, contacting the cells with a chemical reagent capable of permeabilizing or porating the cell membrane. The chemical reagent can, for example, comprise a detergent. The term "detergent" as used herein refers to an amphiphilic (partly hydrophilic/polar and partly hydrophobic/non-polar) surfactant or a mixture of amphiphilic surfactants. Detergents can be broadly categorized according to the charge of their polar portion as "anionic" (negative charge; examples including, but not limited to, alkylbenzenesulfonates and bile acids, such as deoxycholic acid), "cationic" (positive charge; examples including, but not limited to, quaternary ammonium and pyridinium-based detergents), "nonionic" (no charge; examples including, but not limited to, polyoxyethylene/PEG-based detergents such as Tween and Triton, and glycoside-based detergents such as HEGA and MEGA), and "zwitterionic" (no charge due to equal numbers of positive and negative charges on the detergent molecules; examples including, but not limited to, CHAPS and amidosulfobetaine-type detergents). In some embodiments, suitable detergents for permeabilizing the cell, comprise sodium dodedcyl sulfate (SDS), digitonin, leucoperm, saponin, Tween 20, Triton X-100 and additional detergents identifiable to a skilled person. Detergents can be provided at a range of concentrations as will be understood by a skilled person. For example, 0.001%-1% detergent, 0.05%-0.5% detergent, or 0.1%-0.3% detergent can be used for permeabilization (e.g., 0.1% Saponin, 0.2% Tween-20, 0.1-0.5% triton X-100). In some embodiments, the chemical reagent capable of permeabilizing cells can comprise one or more organic fixatives (e.g., acetone, methanol, ethanol) and/or enzymes.

In some embodiments, the same reagent(s) can be used as the fixation reagent and the permeabilization reagent. For example, in some embodiments, the fixation reagent can be organic solvents, such as methanol and acetone. The organic solvents can permeabilize and fix cells at the same time because the organic solvents dissolve lipids from cell membranes making the cells permeable, and also coagulate proteins making the cells fixed. Accordingly, fixing a plurality of cells can generate a plurality of fixed cells also comprising permeabilized cells.

In some embodiments, to permeabilize cells, a cell sample comprising a plurality of cells can be contacted by a permeabilization reagent for a wide range of times, which can depend on the temperature, the nature of the sample, and on the choice of permeabilization reagent(s). For example, a cell sample can be contacted by a permeabilization reagent for about, at least, at least about, at most, at most about 24 hours, 18 hours, 12 hours, 8 hours, 6 hours, 4 hours, 2 hours, 60 minutes, 45 minutes, 30 minutes, 25 minutes, 20 minutes, 15 minutes, 10 minutes, 5 minutes, or 2 minutes, or a number or a range between any two of these values. A cell sample can be contacted by a permeabilization reagent at various temperatures, depending on the protocol and the reagent used. For example, in some embodiments, a cell sample can be contacted by a permeabilization reagent at a temperature ranging from −82° C. to 55° C., including, but are not limited to: 50 to 54° C., 40 to 44° C., 35 to 39° C., 28 to 32° C., 20 to 26° C., 0 to 6° C., −18 to −22° C., and −78 to −82° C. In some embodiments, a cell sample can be contacted by a permeabilization reagent at a temperature of −80° C., −20° C., 4° C., room temperature (e.g., 22-25° C.), 30° C., 37° C., 42° C., or 52° C.

Loading Cells and Barcoded Microcarriers

In some embodiments, the method comprises loading a plurality of fixed cells into a plurality of microwells. The method also comprises loading a plurality of barcoded microcarriers into the plurality of microwells. Loading the barcoded microcarriers and/or the fixed cells can be accomplished, for example, by pumping, drawing, perfusing, or "flowing" different liquid reagents from the inlet through the flow channels of a microfluidic device. Loading the barcoded microcarriers can be performed sequentially (e.g. before or after) or concurrently with loading the fixed cells. In an open well format, loading the fixed cells and/or the barcoded microcarriers can be accomplished by directly adding the cells and/or the barcoded microcarriers to the surface of microarray.

In some embodiments, loading the plurality of fixed cells and/or the plurality of barcoded microcarriers can be performed using partitioning. The term "partitioning" as used herein refers to introducing particles (e.g., cells or barcoded microcarriers) into vessels (e.g., microwells) that can be used to sequester or separate one particle from another. Such vessels are referred to using the noun "partition".

Partitioning can be performed using a variety of methods known to a person skilled in the art, for example, using microfluidics, wells, microwells, multi-well plates, multi-well arrays, and the like. For example, the cells and/or barcoded microcarriers can be diluted and dispensed across a plurality of partitions (e.g. microwells) via the use of flow channels in a microwell array. For example, the cells and/or barcoded microcarriers can be diluted and directly dispensed across a plurality of partitions (e.g. microwells) of an open well format microwell array.

In some embodiments, loading the plurality of fixed cells into a plurality of partitions (e.g. microwells) comprises partitioning the plurality of fixed cells into the plurality of microwells such that a microwell of the plurality of microwells comprises at most one cell (e.g., no cell or a single cell). In some embodiments, loading the plurality of barcoded microcarriers into a plurality of partitions (e.g. microwells) comprises partitioning the plurality of barcoded microcarriers into the plurality of microwells such that a microwell of the plurality of microwells comprises at most one barcoded microcarrier (e.g., no barcoded microcarrier or a single barcoded microcarrier). In some embodiments, the plurality of fixed cells and the plurality of barcoded microcarriers can be co-partitioned by combining the plurality of fixed cells and the plurality of barcoded microcarriers to form a mixture that can be then partitioned into a plurality of microwells.

In some embodiments, partitioning a plurality of fixed cells and/or a plurality of barcoded microcarriers can be performed through the use of fluid flow in a microwell array. For example, the partitioning can comprise flowing one or more solutions comprising a plurality of fixed cells and/or a plurality of barcoded microcarriers, sequentially or concurrently in a mixture, into the plurality of microwells via the inlet port of the microwell array.

Sealing Microwells

In some embodiments, the method comprises sealing the plurality of microwells to produce a sealed microwell array comprising the loaded cells and barcoded microcarriers. For example, in some embodiments, the microwell array can be sealed with a cover to provide microwells having a single cell and one barcoded microcarrier isolated in a microwell. The cover can be a physical structure, including but not limited to a physical structure comprising or being a film, a membrane, a glass slide, or a combination thereof. Non-limiting examples of the physical structure include a single or double-layer of PDMS film or a glass slide (with or without a manual clamp). The physical structure can be permeable, semi-permeable or not permeable. In some embodiments, the physical structure is a nanoporous membrane. In some embodiments, the microwells or the microwell array is not sealed with a nanoporous membrane. The cover can be a fluid barrier. For example, the cover can be an oil to separate and seal the aqueous mixture of cells, microcarriers, and reaction solution. An oil can be utilized if it is chosen to be denser than the aqueous phase of the cell sample such that it can push away all aqueous solution and seal the microwells. But due to surface tension and microdimension of the microwells, the oil cannot flow into the microwells. In some embodiments, the oil is fluorinated hydrocarbon oil. In some embodiments, the cover used to seal the microwells can be a liquid or a gas that is substantially immiscible with the sample fluid in the microwells (e.g., water), thus providing control of surface chemistry and preventing the evaporation of solution inside the channels and cross-contamination between microwells.

In some embodiments, the cover comprises fluorinated fluid. In some embodiments, the cover comprises non-fluorinated fluid (e.g., mineral oil). For example, substances that can be used as a cover include, but are not limited to, fluorocarbons, perfluorocarbons, alkyl and aryl fluorocarbons, halofluorocarbons, fluorinated alcohols, fluorinated oils, liquid fluoropolymers including perfluoropolyethers, perfluorooctyl bromide, perfluorooctylethane, octadecafluorodecahydronaphthalene, 1-(1, 2, 3, 4, 4, 3, 5, 5, 6-undecafluorocyclohexyl)ethonal, $C_6F_{11}C_2H_4OH$, Flourinert (3M), Krytox oils, Fomblin oils, Demnum mineral oil and alkanes. In some embodiments, the oil comprises a fluorinated hydrocarbon oil. In some embodiments, additional substances (e.g., surfactant) can be added to the cover to control the surface tension and wetting properties of the cover fluid as will be understood by a skilled person.

Sealing the microwells can be accomplished by flowing a cover liquid through an inlet of a microwell array. After releasing the molecular barcodes from the microbeads and barcoding the nucleic acid targets, sealing can be removed such that the contents of the cells can be pooled. In some embodiments, sealing can be removed by perfusing a buffer (e.g., saline buffer) from the inlet through the flow channels of the microwell array to push the cover liquid out from the outlet.

In some embodiment, the sealing of the microwells can be accomplished by pressurizing and deforming the top layer of the microfluidic device to generate a physical sealing of the microwells with the top layer. For example, the PDMS top layer of the microfluidic device can be pressed down by a pressure generated by, but not limited to, a mechanical force, a hydrostatic force, a pneumatic force.

Releasing Molecular Barcodes

The method can comprise releasing the molecular barcodes from the microbeads in the sealed microwells. The released molecular barcodes can diffuse through the permeable or porous lipid bilayer membrane into the fixed cells and hybridize to the nucleic acid targets of the fixed cells to initiate the barcoding process, for example without lysing or digesting the cells. In some embodiments, releasing molecular barcodes occurs after the microwells are sealed so as to prevent cross-contamination between microwells.

In some embodiments, releasing the molecular barcodes from the microbeads comprises disrupting the microbeads. For example, the microbeads can be gel beads and when the gel beads are disrupted (e.g., dissolved) the molecular barcodes associated with the gel beads can be released and diffuse into the fixed cells. In some embodiments, releasing the molecular barcodes from the microbeads comprises cleaving the releasable linkers that link the molecular barcodes to the microbeads. The cleavable linkers can be cleaved, digested or degraded under a different set of conditions to release the molecular barcodes. Depending on the structure and nature of the cleavable linkers, the molecular barcodes can be released by, for example, exposing the barcoded microcarriers to an enzyme, a suitable temperature, a suitable pH, light, a chemical agent, sonication, shear stress, or any combination thereof. In some embodiments where a chemical linker is used, cleaving the linker can comprise contacting the barcoded microcarriers with a chemical agent capable of chemically cleaving the chemical linker under a condition for a suitable period of time. In some embodiments where a nucleotide or polynucleotide linker is used, cleaving the linker can comprise contacting the barcoded microcarriers with a restriction enzyme capable of enzymatically cleaving the nucleotide or poly-nucleotide linker under a condition for a suitable period of time.

In some embodiments where a photocleavable linker is used, cleaving the linker comprises exposing the microwells to electromagnetic radiation (e.g., UV light, visible, and near-infrared wavelengths) for a suitable exposure time period. The exact wavelength or wavelength range and exposure time period depend on the specific photocleavable linker and the type of electromagnetic radiation used. For example, the release of the molecular barcodes can occur at a wavelength ranging from about 10 to 400 nm. In some embodiments, the release of the molecular barcodes occurs at a wavelength ranging from about 380 to 780 nm. In some embodiments, the release of the molecular barcodes can occur at a wavelength ranging from about 780 to 1000 nm. The exposure time period can be about, at least, at least about, at most, at most about 2 minutes, 5 minutes, 10 minutes, 15 minutes, 30 minutes, 60 minutes, 90 minutes, 2 hours, or a number or a range between any two of these values.

After the molecular barcodes are released, the microflu-idic device can be incubated at a temperature for a suitable time period (e.g., 30-90 minutes) to allow the released molecule barcodes to diffuse into the permeabilized fixed cells and hybridize to the cellular nucleic acids. For example, the polyT sequence of the oligonucleotides released from the microcarriers will bind to the polyA tail of the mRNAs of the cells. The incubation temperature can be a room temperature (e.g., 22-25° C.). In some embodiments, incubation temperature can be increased to facilitate the diffusion and binding. For example, the incubation tempera-ture can be increased to about 30-50° C., optionally 40-50° C.

Barcode Oligonucleotide Extension

In some embodiments, the method comprises barcoding the nucleic acids (e.g., mRNA targets) associated with the cell. Barcoding the nucleic acids associated with the cell can comprise extending the molecular barcode attached to the barcoded microcarrier and hybridized to the nucleic acid targets (e.g., mRNA targets) using the nucleic acid targets as templates to generate single-stranded barcoded nucleic acids. For example, the barcoded nucleic acids can be generated by reverse transcription using a reverse tran-scriptase. For example, the barcoded nucleic acids can be generated by using a DNA polymerase. Barcoding the nucleic acids associated with the cell can comprise gener-ating double-stranded barcoded nucleic acids from the single-stranded barcoded nucleic acids.

Extending the single-stranded barcoded nucleic acids can comprises extending the single-stranded barcoded nucleic acids using a template switching oligonucleotide. For example, a reverse transcriptase can be used to generate a cDNA by extending a molecular barcode hybridized to an RNA. After extending the molecular barcode to the 5'-end of the RNA, the reverse transcriptase can add one or more nucleotides with cytosine (Cs) bases (e.g., two or three) to the 3'-end of the cDNA. The template switch oligonucleotide (TSO) can include one or more nucleotides with guanine (G) bases (e.g., two or three) on the 3'-end of the TSO. The nucleotides with guanine bases can be ribonucleotides. The guanine bases at the 3'-end of the TSO can hybridize to the cytosine bases at the 3'-end of the cDNA. The reverse transcriptase can further extend the cDNA using the TSO as the template to generate a cDNA with the TSO sequence on its 3'-end. Similarly, a barcoded nucleic acid can include a TSO sequence at its 3'-end.

In some embodiments, reverse transcribing the mRNA hybridized with the molecular barcode to generate barcoded cDNA is performed without lysing or digesting the cells. The molecular barcode released from a microbead can pass through a permeable or porous lipid bilayer membrane (e.g., a cell membrane or a nuclear envelope) of a permeabilized cell and anneal to the RNA within the cell to initiate the barcoding process.

In some embodiments, the method can comprise lysing or digesting the fixed cells after the barcoded nucleic acids are generated and before pooling the barcoded nucleic acids from the plurality of microwells to release the content of the cells. Lysing or digesting the fixed cells can comprise contacting one or more lysis agents with the cells. Examples of lysis agents include bioactive reagents, such as lysis enzymes, or surfactant based lysis solutions including non-ionic surfactants such as TritonX-100 and Tween 20, and ionic surfactants such as sodium dodecyl sulfate (SDS). Lysis methods including, but not limited to, thermal, acous-tic, electrical, or mechanical cellular disruption. Digesting agents include proteinase, such as Serine proteases, Cysteine proteases, Threonine proteases, Aspartic proteases, Gluta-mic proteases, Metalloproteases, or Asparagine peptide lyases.

Pooling Barcoded Nucleic Acids

In some embodiments, the method comprises pooling barcoded nucleic acids from the plurality of microwells after barcoding the nucleic acid targets and before analyzing the barcoded nucleic acids or products thereof. In some embodi-ments, pooling barcoded nucleic acids occurs after generat-ing the double-stranded barcoded nucleic acids. The pooled barcoded nucleic acids can be single-stranded or double-stranded. In some embodiments, the method comprises pooling the barcoded nucleic acids subsequent to extending the molecular barcodes hybridized to the nucleic acid targets associated with a cell to generate the single-stranded bar-coded nucleic acids. The double-stranded barcoded nucleic acids can be generated from single-stranded barcoded nucleic acids in bulk. In some embodiments, the method can comprise pooling the barcoded nucleic acids subsequent to generating the double-stranded barcoded nucleic acids. The double-stranded barcoded nucleic acids can be generated from single-stranded barcoded nucleic acids in the partition.

In some embodiments, the microbeads in the partitions are not pooled (e.g., not removed from the partitions). In some embodiments, the microbeads are pooled from the microwells with the barcoded nucleic acids. The pooled barcoded nucleic acids (e.g., barcoded cDNAs) can be purified and/or amplified prior to sequencing library con-struction. The pooled barcoded nucleic acids with desired length may be selected.

Barcoded Nucleic Acids Amplification

The method can comprise amplifying the barcoded nucleic acid (e.g., barcoded cDNAs) to generate amplified barcoded nucleic acids. Amplifying the barcoded nucleic acids can comprise amplifying the barcoded nucleic acids using polymerase chain reaction (PCR) to generate the amplified barcoded nucleic acids. For example, the molecular barcode can include a first polymerase chain reaction (PCR) primer-binding sequence. The first PCR primer-binding sequence and the TSO sequence can be used to amplify the barcoded nucleic acid, such as a barcoded cDNA. A first primer comprising the sequence of first PCR primer-binding sequence and a second primer comprising a TSO sequence can be used to amplify the barcoded nucleic acid, such as a barcoded cDNA.

Sequencing Library Construction

The barcoded nucleic acids (e.g., barcoded cDNAs or products thereof) can be further processed prior to sequencing to generate processed barcoded nucleic acids. For example, the method can include fragmentation of barcoded nucleic acids, end repair of fragmented barcoded nucleic acids, A-tailing of fragmented barcoded nucleic acids that have been end-repaired to facilitate ligation to adapters, and attaching ligation (e.g., by ligation and/or PCR) with sequencing primer sequences (e.g., a Read 1 sequence and a Read 2 sequence), sample indexes (e.g., short sequences specific to a given sample library), and/or flow cell binding sequences (e.g., P5 and/or P7). Additional PCR amplification can also be performed. This process can also be referred to as sequencing library construction.

In some embodiments, the method comprises fragmenting (e.g., via enzymatic fragmentation, mechanical force, chemical treatment) the barcoded nucleic acids or products thereof to generate fragmented barcoded nucleic acids. Fragmentation can be carried out by any suitable process such as physical fragmentation, enzymatic fragmentation, or a combination of both. For example, the barcoded nucleic acids can be sheared physically using acoustics, nebulization, centrifugal force, hydrodynamics. In some embodiments, the barcoded nucleic acids are fragmented using enzymes such as restriction enzymes (e.g., restriction endonucleases).

Fragmentation can yield fragments of desired size(s) for subsequent sequencing. The desired sizes of the fragmented nucleic acids are determined by the limitations of the next generation sequencing instrumentation and by the specific sequencing application as will be understood by a person skilled in the art. For example, when using Illumina technology, the fragmented nucleic acids can have a length of between about 50 bases to about 1,500 bases. In some embodiments, the fragmented barcoded nucleic acids have about 100 bp to 1,000 bp in length. In some embodiments, the fragmented barcoded nucleic acids have about 400 bp to 700 bp in length.

Fragmented barcoded nucleic acids can undergo end-repair and A-tailing (to add one or more adenine bases) to form an A overhang. This A overhang allows adapter containing one or more thymine overhanging bases to base pair with the fragmented barcode nucleic acids.

Fragmented barcoded nucleic acids can be further processed by adding additional sequences (e.g., adapters) for use in sequencing based on specific sequencing platforms. Adapters can be attached to the fragmented barcoded nucleic acids by ligation using a ligase and/or PCR. For example, fragmented barcoded nucleic acids can be processed by adding sequencing primer sequences. The sequencing primer sequences can comprise a Read 1 sequence and a Read 2 sequence. A double-stranded adapter comprising the primer sequences can be ligated to the fragmented barcoded nucleic acids after, for example, end-repair and A tailing, using a ligase. The adaptor can include one or more thymine (T) bases that can hybridize to the one or more A bases added by A tailing.

The adapter can include platform-specific sequences for fragment recognition by specific sequencing instruments. For example, the adapter can comprise a sequence for attaching the fragmented barcoded nucleic acids to a flow well of Illumina platforms, such as a P5 sequence, a P7 sequence, or a portion thereof. Different adapter sequences can be used for different next generation sequencing instruments as will be understood by a person skilled in the art.

In some embodiments, sequencing the barcoded nucleic acids or products thereof, comprises sequencing products of the barcoded nucleic acids. Products of the barcoded nucleic acids can include the processed nucleic acids generated by any step of the sequencing library construction process, such as amplified barcoded nucleic acids, fragmented barcoded nucleic acids, fragmented barcoded nucleic acids comprising additional sequences such as the sequencing primer sequences and/or adapter sequences described herein.

Analysis

The method can comprise analyzing the barcoded nucleic acids (e.g. barcoded cDNAs) or products thereof. The methods and systems disclosed herein can, in some embodiments, allow a high throughput single-cell analysis of barcoded nucleic acids from about 100 cells to about 50,000 cells.

In some embodiments, analyzing the barcoded nucleic acids or products thereof comprises sequencing the barcoded nucleic acids or products thereof to obtain sequence information. As used herein, a "sequence" can refer to the sequence, a complementary sequence thereof (e.g., a reverse, a compliment, or a reverse complement), the full-length sequence, a subsequence, or a combination thereof. The nucleic acids sequences of the barcoded nucleic acids can each comprise a sequence of a molecular barcode (e.g., the cell barcode and the UMI) and a sequence of a nucleic acid target associated with a cell or a reverse complement thereof.

The barcoded nucleic acids can be sequenced using any suitable sequencing method identifiable to a person skilled in the art. For example, sequencing the barcoded nucleic acids can be performed using high-throughput sequencing, pyrosequencing, sequencing-by-synthesis, single-molecule sequencing, nanopore sequencing, sequencing-by-ligation, sequencing-by-hybridization, next generation sequencing, massively-parallel sequencing, primer walking, and any other sequencing methods known in the art and suitable for sequencing the barcoded nucleic acids generated using the methods herein described.

The obtained nucleic acid sequences can be subjected to any downstream post-sequencing data analysis as will be understood by a person skilled in the art. The sequence data can undergo a quality control process to remove adapter sequences, low-quality reads, uncalled bases, and/or to filter out contaminants. The high-quality data obtained from the quality control can be mapped or aligned to a reference genome or assembled de novo.

In some embodiments, analyzing the barcoded nucleic acids (cDNAs) or products thereof comprises determining a profile (e.g., an expression profile) of each of one or more nucleic acid targets of the nucleic acid targets associated with the cell using a number of UMIs with different sequences associated with each of the mRNA targets in the sequencing information. A profile can be a transcriptome profile. The expression profile can comprise an absolute abundance or a relative abundance. The expression profile can comprise an mRNA expression profile. The profile can be a profile of one cell. The profiles can be profiles of two cells of different kinds.

In some embodiments, analyzing the barcoded nucleic acids comprises determining a number of amplified barcoded cDNAs of each of one or more the mRNA targets using a number of UMIs with different sequences associated with each of the mRNA targets in the sequencing information.

In some embodiments, analyzing the sequencing information can comprise determining sequences of the nucleic acid target, or a portion thereof, associated with UMIs with different sequences. For example, analyzing the sequencing information can include determining presence of one or more mutations (such as an insertion, a deletion, or a substitution) and an abundance (e.g., frequency or occurrence) of each of the mutation. The mutations can be, for example, related to cancer. For example, analyzing the sequencing information can include determining presence of each of one or more variants of a virus and an abundance (e.g., frequency or occurrence) of each variant. The variants can, for example, affect the transmissibility of the virus or affect the severity of the disease caused by the virus. For example, analyzing the sequencing information can include determining the sequences of genes of interest (e.g., TCR alpha and TCR beta) in the cell.

Systems and Kits

Disclosed herein also include compositions, systems, and kits for single-cell profiling or single cell analysis. In some embodiments, a composition for single cell analysis comprises a plurality of barcoded microcarriers of the present disclosure. In some embodiments, a kit for single cell analysis comprises a composition comprising a plurality of barcoded microcarriers of the present disclosure. The kit can comprise instructions of using the composition for single cell sequencing or single cell analysis.

Disclosed herein includes a system for performing the high throughput single-cell mRNA profiling method disclosed herein. In some embodiments, the system comprises a microwell array comprising the plurality of microwells, the plurality of barcoded microcarriers, a means for sealing the microwell array, a means for cleaving the releasable linkers to release the molecular barcodes from the microbeads, and a means for generating the barcoded cDNAs. In some embodiments, the system can also comprise a means for lysing or digesting the cells to release the barcoded cDNAs. In some embodiments, the system can comprise a means for collecting the barcoded cDNAs. In some embodiments, the system can comprise a means for sequencing the barcoded cDNAs or the amplified barcoded cDNAs.

EXAMPLES

Some aspects of the embodiments discussed above are disclosed in further detail in the following examples, which are not in any way intended to limit the scope of the present disclosure.

Example 1

MX-CDB scRNA-seq Workflow

The MX-CDB scRNA-seq method of the present invention utilizes a microfluidic device with a microwell array as the platform to isolate single cells and barcoded microcarriers. The microwell arrays are made from polydimethylsiloxane (PDMS). The dimension of the microwells is determined by the size of the barcoded microcarriers and the size of cells. Barcoded microcarriers made from polymeric microbeads with diameter of about 35 μm were used. Microwell arrays used herein are with about 45 μm in diameter and about 45 μm in depth to guarantee only a single bead in contact with isolated cells in one microwell. The choice of dimensions also facilitates the collection of released cDNA from the digested cells in liquid solution after the reverse transcription process.

In this study, a microwell array having 35,000 microwells was used to sequence approximately 1,000-3,000 cells in a single run where the arrays are loaded with a well occupancy rate of about 5% to about 10% to reduce cell doublets or higher multiples in one microwell.

Microfluidic Device Fabrication

The PDMS microfluidic device is assembled by a silicone rubber film with defined flow channel sandwiched between a PDMS microwell array substrate and a UV penetrable glass slide top. The PDMS microwell array substrate is replicated from a Silicon mold with column array on top by soft lithography. A thin layer of patterned silicone rubber film (about 500 um in thickness) with defined flow channel is placed on the top of the PDMS microwell array substrate. A UV penetrable glass slide having two through holes used as the inlet and the outlet is placed on the top the silicone rubber film. The inlet and the outlet match the two ends of the flow channel. Then liquid can be perfused from the inlet through the flow channel to the outlet. In this case, the samples and reagents can be delivered to the microwell array, and the waste liquid can be pushed out from the microfluidic device and be removed.

Microfluidic Device Priming

The microfluidic device priming is performed before usage to increase the surface hydrophilicity and avoid trapping of air bubbles in the microfluidic device. Ethanol (100%) is used to flush the surface and remove air bubbles trapped in the microwells. Then priming solution is perfused into the flow channel to treat the microwell array for about 30 minutes at room temperature. After priming, the microfluidic flow channel is perfused with phosphate buffered saline (PBS) to remove the priming solution.

Preparation of Cells

The NIH/3T3 mouse fibroblast cells and K562 human leukemia cells were cultured in DMEM with 10% Fetal Bovine Serum (FBS) and penicillin and streptomycin (PS) at 37° C. with 5% $CO_2$. Cells were collected from cell culture flask and centrifuged at 500 g for 3 minutes to form cell pellet. The cell pellet was resuspended in 1 mL of PBS with RNase Inhibitor. The cell suspension was passed through a 40 um cell strainer to remove cell clusters. Then the cells were counted under hemocytometer to dilute to $1\times10^5$ cells/mL. For mixed cell experiments, 3T3 cells and K562 cells were mixed at 1:1 ratio.

Cell Fixation

Cells were collected from cell culture flasks and centrifuged at 500 g for about 3 minutes to form a cell pellet. The cell pellet was resuspended in 1 mL of 4% para formaldehyde solution with RNase inhibitor. The cells were allowed about 10 minutes for cell fixation. After fixation, 0.5% Trition X-100 was added to the cell solution to permeabilize the cells, allowing about 10 minutes for permeabilization. The cells were centrifuged at 500 g for about 3 minutes and resuspended in PBS with RNase inhibitor. The cell suspension was passed through a 40 μm cell strainer to remove cell clusters. The cells were counted under a hemocytometer to dilute the sample to a concentration of about $1 \times 10^5$ cells/mL.

Cell Loading

Figure 7A:
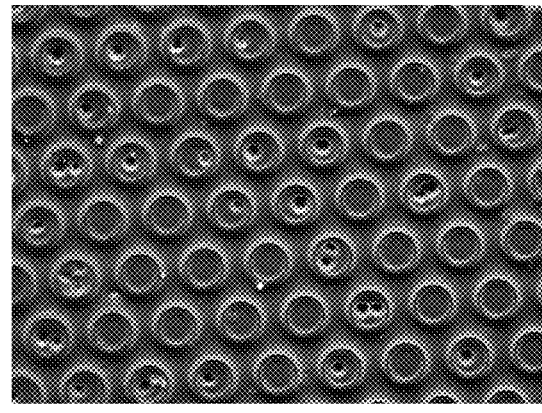
FIG. 7A shows that the microwell array is loaded with about 10% single cell coverage of the microwells.

100 μL of the cell suspension was pipetted into the inlet of the microfluidic device to fill the flow channel. Excess liquid was removed from both the inlet and the outlet of the microfluidic device to stop the flow inside the flow channel. The cells in the suspension were allowed to gradually precipitate (settle) into the microwells due to the gravity. After about 2 minutes, PBS was flushed through the flow channel to remove excess cells that had not precipitated (settled) into a microwell (FIG. 7A).

Bead Loading

Figure 7B:
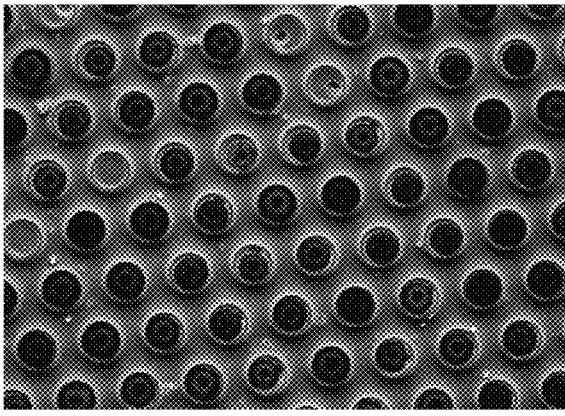
FIG. 7B shows that the microwell array is loaded with microbeads to ensure only one microbead in one microwell.

Barcoded microbeads, also called barcoded microcarriers, at a concentration of about 80,000 microbeads in 50 μL of PBS solution, were slowly loaded into the microfluidic device with a pipette to cover the flow channel halfway. Next, 100 μL PBS was slowly loaded into the microfluidic device to completely cover the entire flow channel with barcoded microbeads. It is important to ensure that about >80%, or even >than 90% of the microwell arrays contain at least one microbead. Excess beads were washed out with PBS (FIG. 7B).

Oligonucleotide Cleavage

After bead loading, Reverse Transcription (RT) buffer, Maxima H minus kit obtained from Thermo Fisher Scientific, was used to flush the flow channel once, and then RT mixer with a template switch primer was added to the flow channel. Next, 100 μL Fluorinert™ oil, which is a fluorinated hydrocarbon oil, was added into the microfluidic device to seal the microwells. The extra liquid at both the inlet and the outlet was removed to stop the flow inside the flow channel.

The microfluidic device was exposed to 300-350 nm near UV-light at a distance of about 5 cm for about 15 minutes to cleave the linkage between the oligonucleotides to the microbeads. The microfluidic device was then allowed to stand at room temperature for about 1 hour, to allow for oligonucleotide diffusion and mRNA capture.

Reverse Transcription And Template Switch

After mRNA capture, the microfluidic device was incubated at 42° C. for about 90 minutes to allow in situ reverse transcription and addition of template switch primer to the cDNA. To prevent the evaporation of solution inside the channels, the entire device was kept inside a sealed wet chamber.

After completion of the reverse transcription reaction, saline-sodium citrate (SSC) buffer with RNase inhibitor was perfused into the flow channel to remove the sealing oil and excess reaction solution.

Cell Digestion

Before loading cell digestion buffer, PBS with Trition X-100 and RNase inhibitor was perfused through device. Next, 100 μl of cell digestion buffer, a phosphate buffer with proteinase, was added into the flow channel to digest the fixed cells at 55° C. for about 2 hours to release the cDNA. The resulting lysate containing the released cDNA was collected from the microfluidic device.

Purification and PCR Amplification

The collected lysate from the microfluidic device has floating cDNAs. The cDNAs in the collected cell lysate were purified with magnetic beads to capture the floating cDNAs in the lysate to the magnetic beads. cDNAs with desirable sequence length (i.e., ~1000 bp) was selectively captured by magnetic beads. Then the magnetic beads with selected cDNAs was mixed with PCR solution and PCR was carried out to amplify the captured cDNAs.

Purification and Bioanalyzer Analysis

After PCR, the product with amplified cDNAs was purified by magnetic beads again to select the desirable sequences with 1000 bp in length. Then Fluorometer was used to measure the cDNA concentration in the purified solution and the Agilent Bioanalyzer 2100 was used to characterize the quality of the purified solution.

Figure 8:
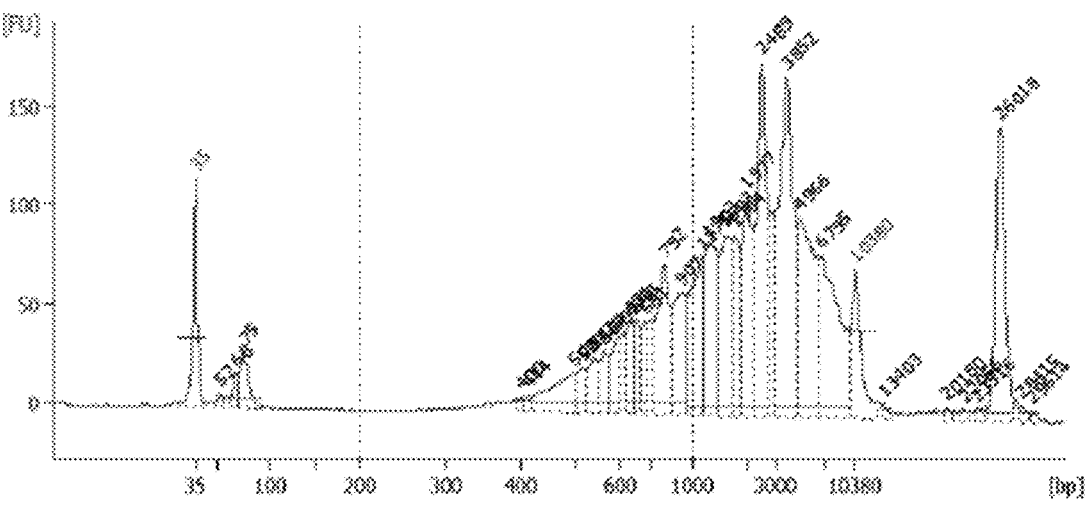
FIG. 8 shows quality of the purified cDNA solution after PCR amplification.

In one case, the cDNA concentration of the PCR product is about 16 ng/ul. The Quality of the purified cDNA solution of PCR product is shown in FIG. 8.

Library Construction and Sequencing

Figure 9:
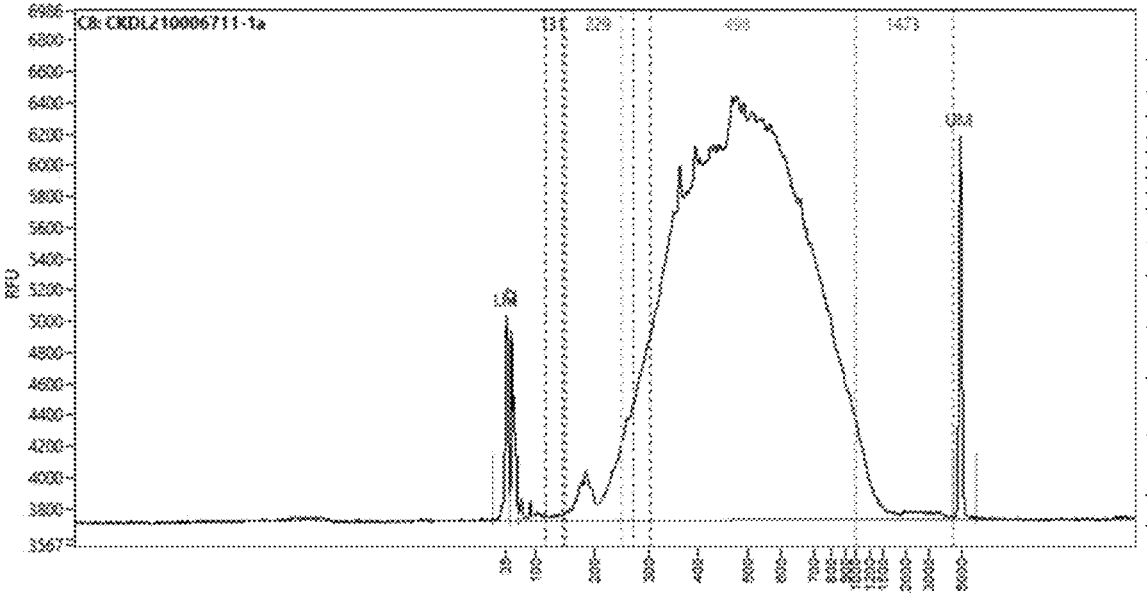
FIG. 9 shows quality of the purified libraries.

The cDNA in the purified solution was then inputted for standard Nextera tagmentation and amplification reactions to construct libraries for sequencing. Custom primers instead of the i5 index primer and the i7 index primer were used to amplify only those fragments containing the cell barcodes and UMIs. The library product was then purified again using magnetic beads. The cDNA concentration of the libraries was measured by Fluorometer and the quality of the libraries was characterized by Labchip GXII Touch HT machine (FIG. 9). The libraries were sequenced on a NovaSeq 6000 sequencer.

Sequencing Data Analysis

Transcriptome alignment including barcode/UMI identification was performed by using DropSeq tools. In brief, the Read 2 sequencing data include PCR primer, cell barcode and UMI sequences, while the Read 1 sequencing data contain the transcript information of captured mRNA. The sequence data were filtered with the PCR primer sequence to remove the incorrect sequences. Then, the filtered reads were aligned to reference transcriptome of the corresponding species (mouse; human; human-mouse mix) to extract gene expression matrix.

Figure 10:
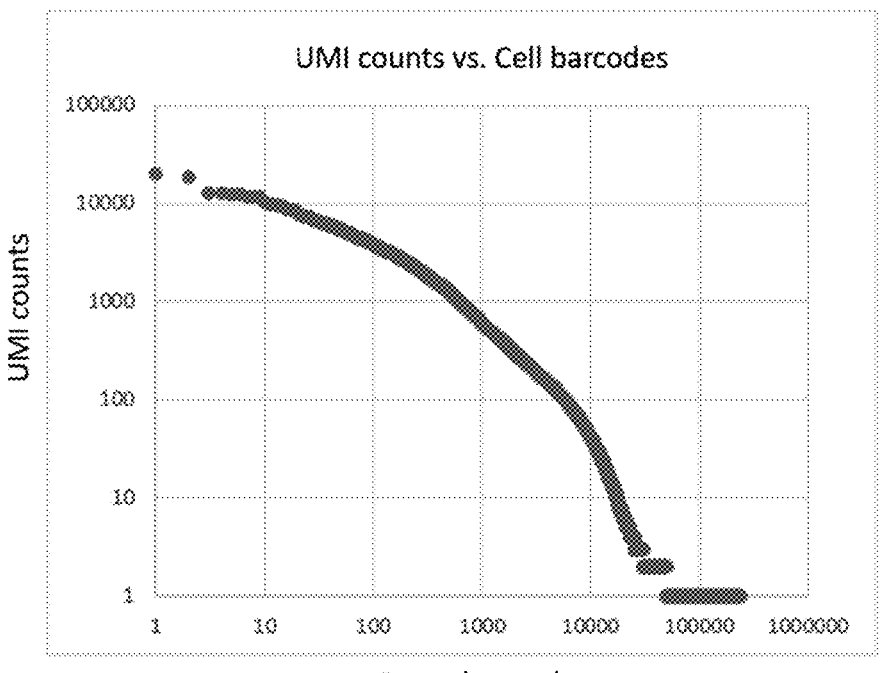
FIG. 10 shows the UMI count vs. cell barcode number.
Figure 11:
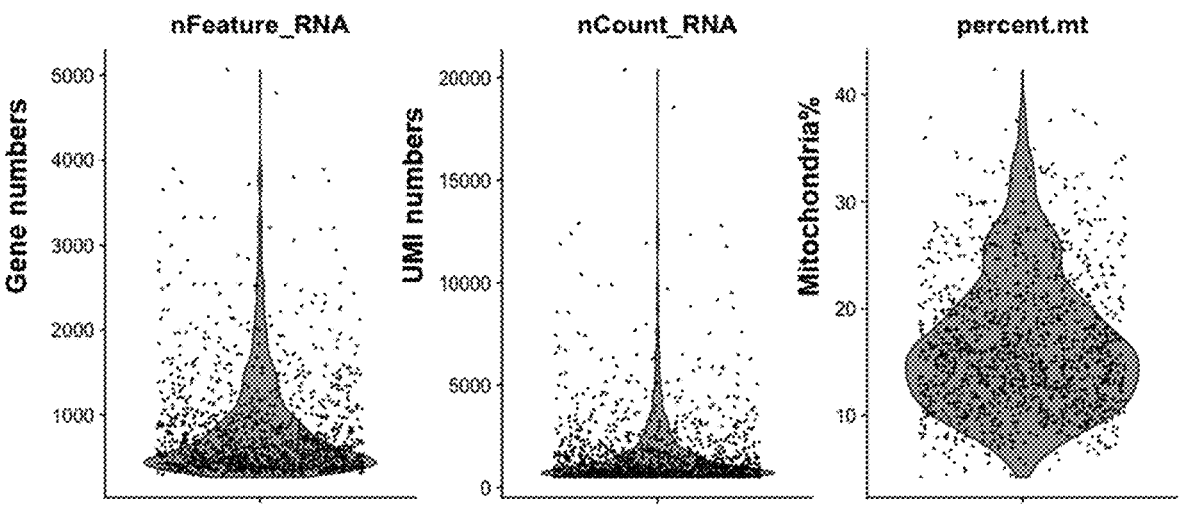
FIG. 11 shows a violin plot of the gene number, UMI number, and mitochondria percentage distribution of determined cells.

Further data analysis was performed by using Seurat. The cell number was determined by selecting the cells with: (1) UMI number is larger than 500; (2) gene number is between 500 and 8000; and (3) Reads are larger than 10000. In this experiment, the estimated cell number is about 1200, with median genes about 600 and median UMI is about 600. The UMI count vs. cell barcode number is shown in FIG. 10. The Violin plots of the gene number, UMI number, and mitochondria percentage distribution of determined cells is shown in FIG. 11.

Example 2

Preparation of Cells

The NIH/3T3 mouse fibroblast cells and U-87 human glioblastoma cells were cultured in DMEM with 10% Fetal Bovine Serum (FBS) and penicillin and streptomycin (PS) at 37° C. with 5% $CO_2$. For mixed cell experiments, 3T3 cells and U-87 cells were mixed at 1:1 ratio.

Cell Fixation

Cells were dissociated with Trypsin in the cell culture flask. Once the cells started dissociating, a fixation mixture (Glycerol, Acetic Acid, and 75% NAC) was loaded into the cell culture flask. The cells were fixed at room temperature for 20 minutes before adding Methanol and incubating at 4° C. for 20 minutes for permeabilization. Then the collected cells were centrifuged at 1000 g for 5 minutes to form a cell pellet. The cell pellet was resuspended in PBS with RNase inhibitor. The cell suspension was passed through a 40 μm cell strainer to remove cell clusters. The cells were counted under a hemocytometer to dilute the sample to a concentration of about $1\times10^5$ cells/mL.

Cell Loading

100 μL of the cell suspension was pipetted into the inlet of the microfluidic device to fill the flow channel. Excess liquid was removed from both the inlet and the outlet of the microfluidic device to stop the flow inside the flow channel. The cells in the suspension were allowed to gradually precipitate (settle) into the microwells due to the gravity. After about 2 minutes, PBS was flushed through the flow channel to remove excess cells that had not precipitated (settled) into a microwell.

Bead Loading

Barcoded microbeads, also called barcoded microcarriers, at a concentration of about 80,000 microbeads in 50 μL of PBS solution, were slowly loaded into the microfluidic device with a pipette to cover the flow channel halfway. Next, 100 μL PBS was slowly loaded into the microfluidic device to completely cover the entire flow channel with barcoded microbeads. It is advantageous to ensure that about >80%, or even >than 90% of the microwell arrays contain at least one microbead. Excess beads were washed out with PBS.

Oligonucleotide Cleavage

After bead loading, Reverse Transcription (RT) buffer, Maxima H minus kit obtained from Thermo Fisher Scientific, was used to flush the flow channel once, and then RT mixer was added to the flow channel. Next, 100 μL Fluorinert™ oil, which is a fluorinated hydrocarbon oil, was added into the microfluidic device to seal the microwells. The extra liquid at both the inlet and the outlet was removed to stop the flow inside the flow channel.

The microfluidic device was exposed to 300-350 nm near UV-light at a distance of about 5 cm for about 15 minutes to cleave the linkage between the oligonucleotides to the microbeads. The microfluidic device was then allowed to stand at room temperature for about 1 hour, to allow for oligonucleotide diffusion and mRNA capture.

Reverse Transcription and Template Switch

After mRNA capture, the microfluidic device was incubated at 42° C. for about 90 minutes to allow in situ reverse transcription. To prevent the evaporation of solution inside the channels, the entire device was kept inside a sealed wet chamber.

After completion of the reverse transcription reaction, saline-sodium citrate (SSC) buffer with RNase inhibitor was perfused into the flow channel to remove the sealing oil and excess reaction solution.

Cell Digestion

Before loading cell digestion buffer, PBS with Trition X-100 and RNase inhibitor was perfused through device. Next, 100 μl of cell digestion buffer, a phosphate buffer with proteinase, was added into the flow channel to digest the fixed cells at 55° C. for about 2 hours to release the cDNAs. The resulting lysate containing the released cDNAs was collected from the microfluidic device.

Purification, Template Switch and PCR Amplification

The collected lysate from the microfluidic device has floating cDNAs. The cDNAs in the collected cell lysate were purified with magnetic beads to capture the floating cDNAs in the lysate to the magnetic beads. cDNAs with desirable sequence length (i.e., ~1000 bp) was selectively captured by magnetic beads. Then the magnetic beads with selected cDNAs was mixed with template switch mixer and incubate at room temperature for 30 minutes and then at 42° C. for 90 minutes with mixing. After template switch, the magnetic beads were transferred into a PCR solution to carry out PCR amplification of the captured cDNAs.

Purification and Bioanalyzer Analysis

After PCR, the product with amplified cDNAs was purified by magnetic beads again to select the desirable sequences with ~1000 bp in length. Then Fluorometer was used to measure the cDNA concentration in the purified solution and the Agilent Bioanalyzer 2100 was used to characterize the quality of the purified solution.

Figure 12:
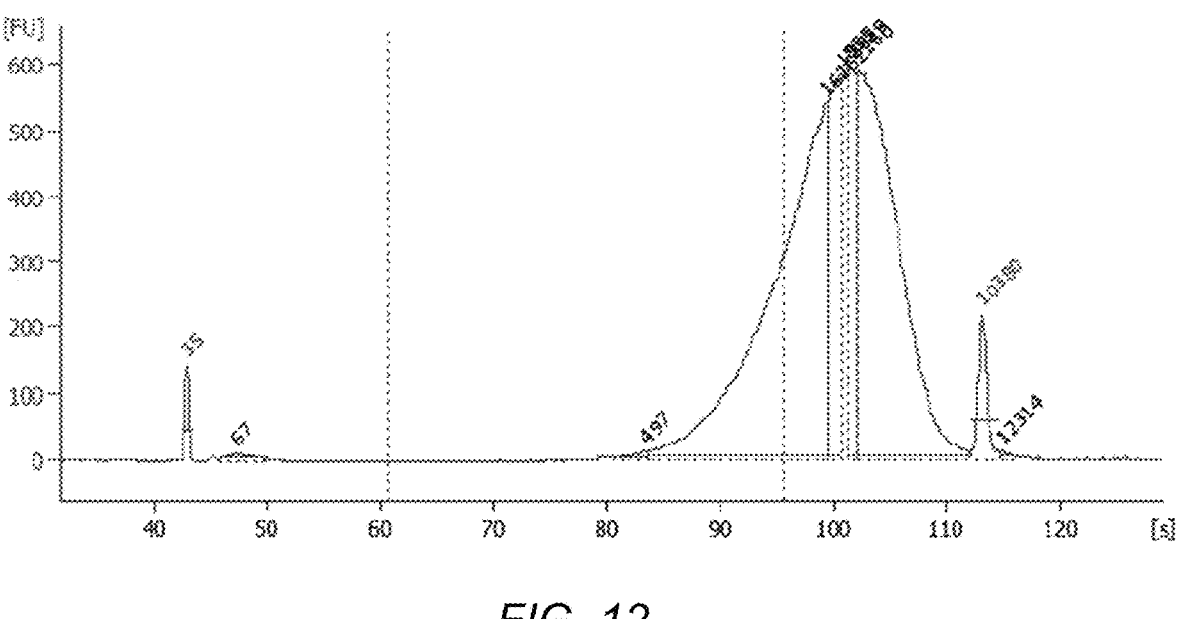
FIG. 12 shows quality of the purified cDNA solution after PCR amplification.

In one case, the cDNA concentration of the PCR product is about 69 ng/ul. The Quality of the purified cDNA solution of PCR product is shown in FIG. 12.

Library Construction and Sequencing

Figure 13:
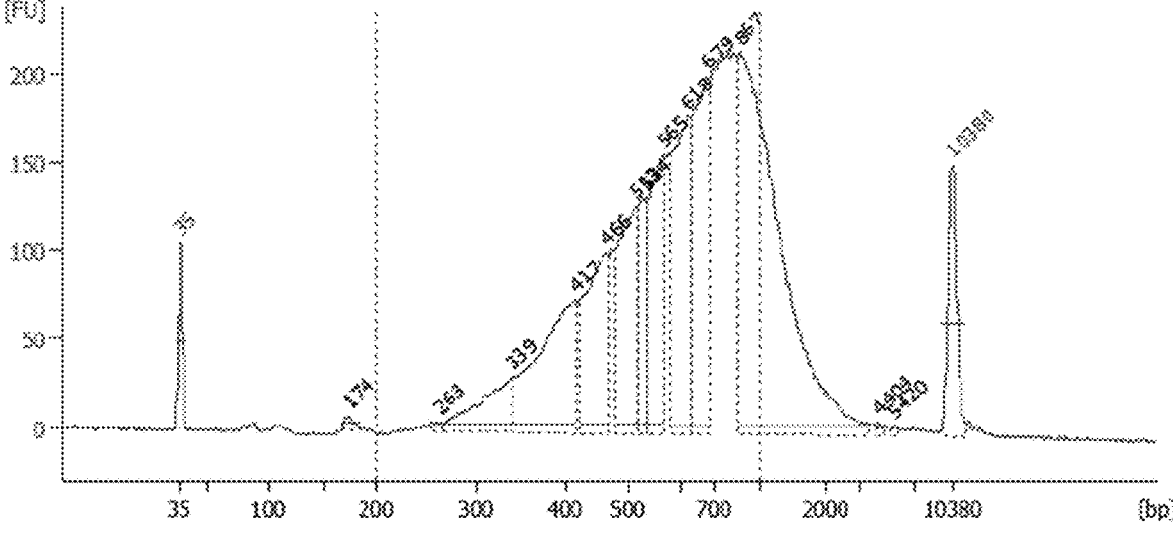
FIG. 13 shows quality of the purified libraries.

The cDNA in the purified solution was then inputted for standard Nextera tagmentation and amplification reactions to construct libraries for sequencing. Custom primers instead of the i5 index primer and the i7 index primer were used to amplify only those fragments containing the cell barcodes and UMIs. The library product was then purified again using magnetic beads. The cDNA concentration of the libraries was measured by Fluorometer and the quality of the libraries was characterized by the Agilent Bioanalyzer 2100 (FIG. 13). The libraries were sequenced on a NovaSeq 6000 sequencer.

Sequencing Data Analysis

Transcriptome alignment including barcode/UMI identification was performed by using DropSeq tools. In brief, the Read 2 sequencing data include PCR primer, cell barcode and UMI sequences, while the Read 1 sequencing data contain the transcript information of captured mRNA. The sequence data were filtered with the PCR primer sequence to remove the incorrect sequences. Then, the filtered reads were aligned to reference transcriptome of the corresponding species (mouse; human; human-mouse mix) to extract gene expression matrix.

Figure 14:
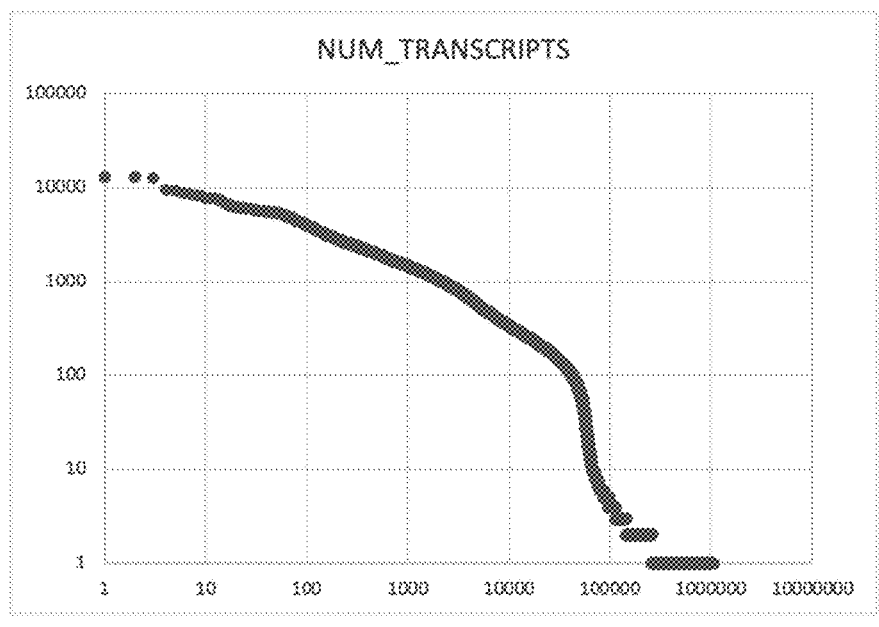
FIG. 14 shows the UMI count vs. cell barcode number.
Figure 15:
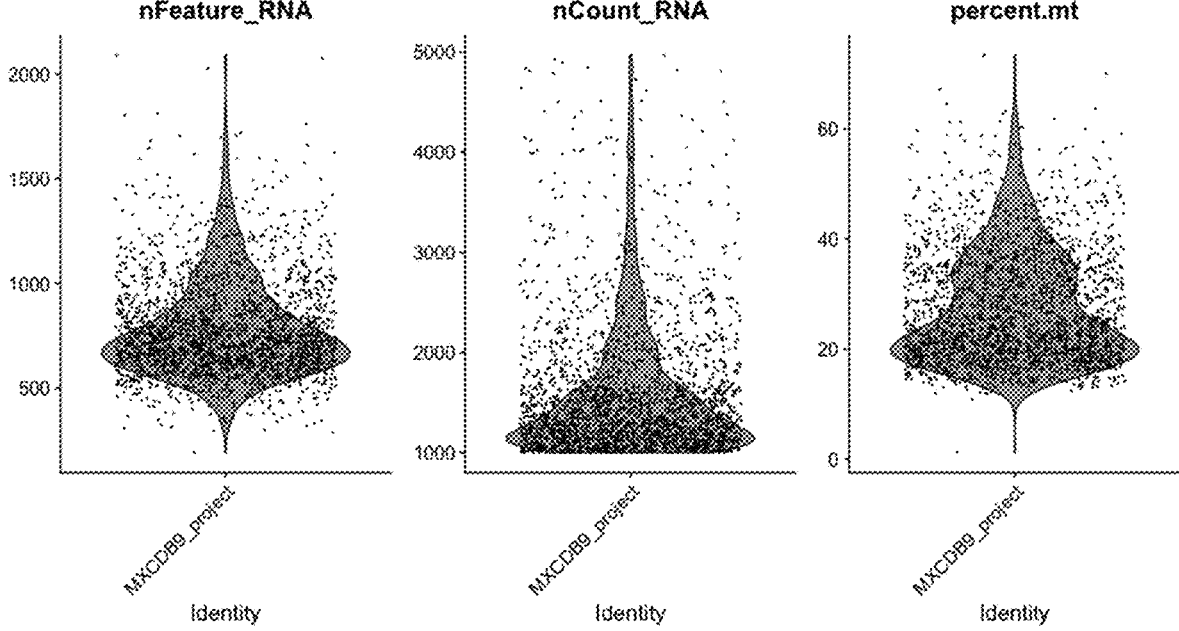
FIG. 15 shows a violin plot of the gene number, UMI number, and mitochondria percentage distribution of determined cells.

Further data analysis was performed by using Seurat. The cell number was determined by selecting the cells with: (1) UMI number is larger than 1000; (2) gene number is between 500 and 8000; and (3) Reads are larger than 10000. In this experiment, the estimated cell number is about 2200, with median genes about 700 and median UMI is about 1400. The UMI count vs. cell barcode number is shown in FIG. 14. The Violin plots of the gene number, UMI number, and mitochondria percentage distribution of determined cells is shown in FIG. 15.

Terminology

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for single-cell RNA profiling, comprising:
loading a plurality of permeabilized fixed cells into a plurality of microwells;

loading a plurality of barcoded microcarriers into the plurality of microwells, wherein at least 5% of the plurality of microwells each is loaded with one of the plurality of permeabilized fixed cells and one of the plurality of barcoded microcarriers, and wherein each of the plurality of barcoded microcarriers comprises:

a microbead, a plurality of molecular barcodes each comprising an identical cell barcode, a unique molecule identifier (UMI) different across the plurality of molecular barcodes, a PCR handle, and a poly-T sequence capable of hybridizing to poly-A tails of messenger ribonucleic acid (mRNA) targets of the plurality of permeabilized fixed cells, and a plurality of releasable linkers each associated with the microbead and linked with one of the plurality of molecular barcodes;

releasing the molecular barcodes from the microbeads in the microwells;

diffusing the molecular barcodes into the permeabilized fixed cells and hybridizing the molecular barcodes to mRNA targets of the permeabilized fixed cells therein at a first temperature from 22° C. to 50° C. for at least 30 minutes;

reverse transcribing in the permeabilized fixed cells the mRNA hybridized with the molecular barcode to generate barcoded complementary deoxyribonucleic acids (cDNAs) without lysing or digesting the cells at a second temperature different from the first temperature;

pooling the barcoded cDNAs from the plurality of microwells; and analyzing the barcoded cDNAs or products thereof.

2. The method of claim 1, further comprising sealing the plurality of microwells.

3. The method of claim 2, wherein sealing the plurality of microwells comprises sealing the plurality of microwells with a physical structure or an oil.

4. The method of claim 1, further comprising amplifying the barcoded cDNAs and sequencing the amplified barcoded cDNAs or products thereof to obtain sequence information.

5. The method of claim 4, wherein analyzing the barcoded cDNAs or products thereof comprises determining an expression profile of each of the mRNA targets using a number of UMIs with different sequences associated with each of the mRNA targets in the sequence information.

6. The method of claim 4, wherein analyzing the barcoded cDNAs comprises determining a number of amplified barcoded cDNAs of each of the mRNA targets using a number of UMIs with different sequences associated with each of the mRNA targets in the sequence information.

7. The method of claim 1, wherein at least 75% of the plurality of microwells each is loaded with one of the plurality of permeabilized fixed cells and one of the plurality of barcoded microcarriers.

8. The method of claim 1, further comprising generating the plurality of permeabilized fixed cells using chemical fixation.

9. The method of claim 1, wherein the microbead is a polymeric microbead, a gel microbead, or a magnetic microbead.

10. The method of claim 1, wherein the plurality of permeabilized fixed cells comprises eukaryotic cells, prokaryotic cells, cells infected with a virus, or a combination thereof.

11. The method of claim 1, wherein each of plurality of releasable linkers is releasably associated with the microbead, releasably linked with the one of the plurality of molecular barcodes, or both.

12. The method of claim 1, wherein releasing the molecular barcodes from the microbeads comprises cleaving the releasable linkers.

13. The method of claim 1, wherein the 5' end of the molecular barcode is linked with the releasable linker.

14. The method of claim 1, wherein the molecular barcode comprises from the 5' end to the 3' end, the PCR handle, the cell barcode, the UMI, and the poly-T sequence or the PCR handle, the UMI, the cell barcode, and the poly-T sequence.

15. The method of claim 1, further comprising lysing or digesting the permeabilized fixed cells after the barcoded cDNAs are generated and before pooling the barcoded cDNAs from the plurality of microwells.

16. The method of claim 1, wherein each of the plurality of microbead has a diameter of 10 μm to 70 um.

17. The method of claim 1, wherein barcoded cDNAs from 100 cells to 50,000 cells are analyzed.

18. The method of claim 1, wherein at least 10% of the plurality of microwells each is loaded with one of the plurality of permeabilized fixed cells and one of the plurality of barcoded microcarriers.

19. The method of claim 1, wherein 10%-75% of the plurality of microwells each is loaded with one of the plurality of permeabilized fixed cells and one of the plurality of barcoded microcarriers.

* * * * *